(12) United States Patent
Lee et al.

(10) Patent No.: US 9,675,603 B2
(45) Date of Patent: Jun. 13, 2017

(54) SOLID PHARMACEUTICAL COMPOSITIONS OF PPARγ MODULATOR

(75) Inventors: Kathleen M. Lee, Palo Alto, CA (US); Linda Higgins, Palo Alto, CA (US); Dennis Lanfear, Portola Valley, CA (US)

(73) Assignee: InteKrin Therapeutics, Inc., Los Altos, CA (US)

(*) Notice: Subject to any disclaimer, the term of this patent is extended or adjusted under 35 U.S.C. 154(b) by 112 days.

(21) Appl. No.: 13/824,776

(22) PCT Filed: Sep. 19, 2011

(86) PCT No.: PCT/US2011/052100
§ 371 (c)(1),
(2), (4) Date: Jun. 3, 2013

(87) PCT Pub. No.: WO2012/040082
PCT Pub. Date: Mar. 29, 2012

(65) Prior Publication Data
US 2013/0243865 A1 Sep. 19, 2013

Related U.S. Application Data

(60) Provisional application No. 61/384,991, filed on Sep. 21, 2010.

(51) Int. Cl.
| | | |
|---|---|---|
| *A61K 31/47* | (2006.01) | |
| *A61K 31/497* | (2006.01) | |
| *A61K 9/14* | (2006.01) | |
| *A61K 9/16* | (2006.01) | |
| *A61K 9/20* | (2006.01) | |
| *A61K 9/48* | (2006.01) | |
| *A61K 31/18* | (2006.01) | |

(52) U.S. Cl.
CPC ............ *A61K 31/47* (2013.01); *A61K 9/1623* (2013.01); *A61K 9/1635* (2013.01); *A61K 9/1652* (2013.01); *A61K 9/2018* (2013.01); *A61K 9/2027* (2013.01); *A61K 9/2054* (2013.01); *A61K 9/4858* (2013.01); *A61K 9/4866* (2013.01); *A61K 31/18* (2013.01); *Y10T 428/2982* (2015.01)

(58) Field of Classification Search
CPC ...... A61K 31/47; A61K 31/18; A61K 9/1623; A61K 9/1652; A61K 9/2018; A61K 9/2027
See application file for complete search history.

(56) References Cited

U.S. PATENT DOCUMENTS

| | | | |
|---|---|---|---|
| 7,223,761 B2 | 5/2007 | Kruk et al. | |
| 2002/0169185 A1 | 11/2002 | McGee et al. | |
| 2003/0139390 A1 | 7/2003 | McGee et al. | |
| 2005/0065183 A1* | 3/2005 | Nandi et al. | 514/317 |
| 2007/0293536 A1 | 12/2007 | Kruk et al. | |
| 2008/0020046 A1* | 1/2008 | Dawson | A61K 9/167 424/489 |
| 2009/0074862 A1* | 3/2009 | Schioppi | A61K 9/2009 424/465 |
| 2010/0087481 A1 | 4/2010 | Lee | |
| 2013/0245024 A1* | 9/2013 | Lanfear et al. | 514/249 |

FOREIGN PATENT DOCUMENTS

WO 2009-111078 A2 9/2009

OTHER PUBLICATIONS

International Search Report for corresponding PCT application No. PCT/US2011/052100 published Mar. 29, 2012.

* cited by examiner

*Primary Examiner* — Mina Haghighatian
(74) *Attorney, Agent, or Firm* — Wood, Phillips, Katz, Clark & Mortimer

(57) ABSTRACT

Provided are pharmaceutical compositions in solid form comprising a selective modulator of PPAR-γ suitable for oral dosage to treat subjects having PPAR-γ mediated conditions. Provided further are methods of manufacturing the compositions, and methods of treating a PPAR-γ mediated condition.

16 Claims, 7 Drawing Sheets

Figure 1:
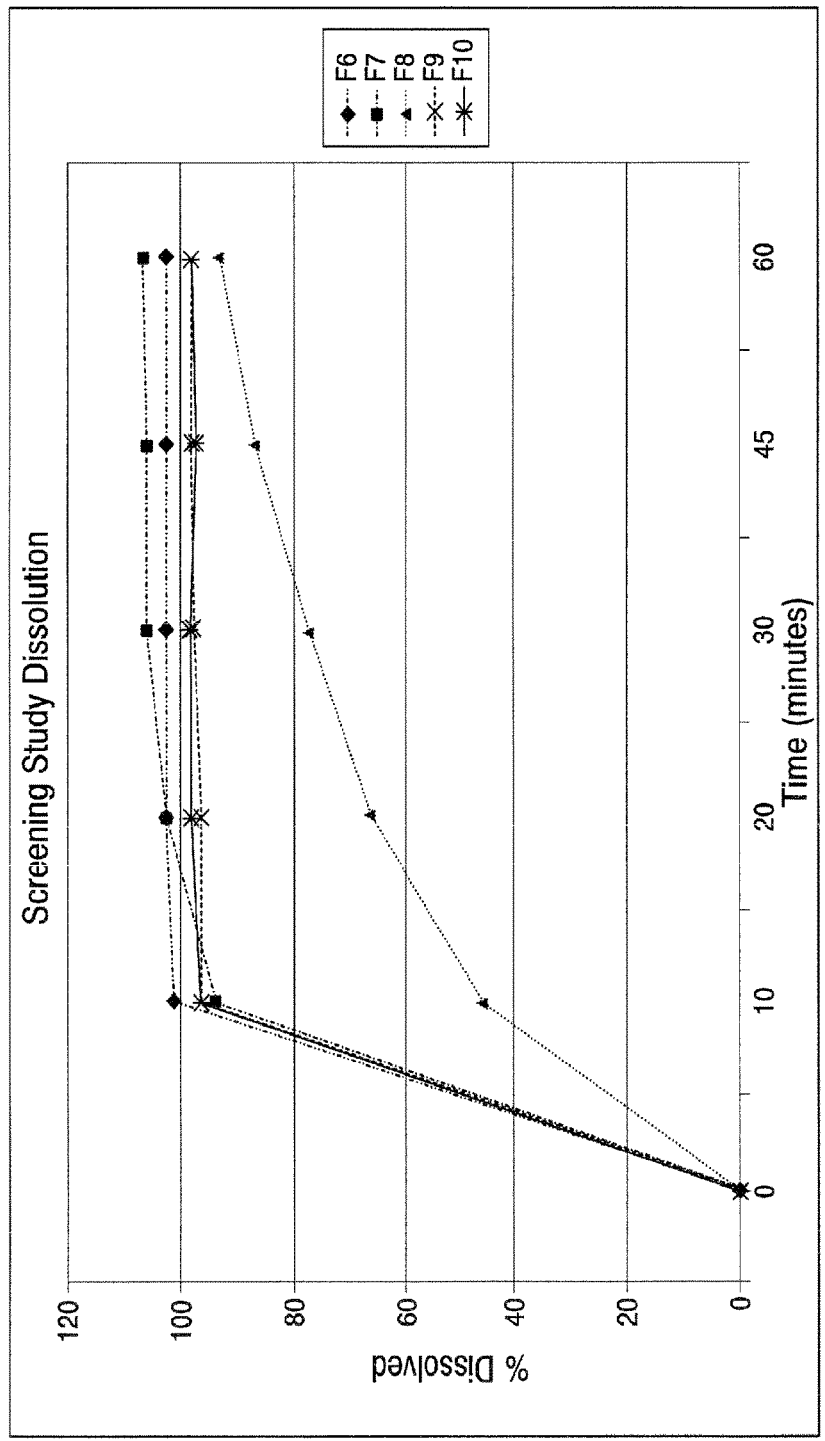

Error bars are standard deviations. N=3 (except N = 2 for F4).

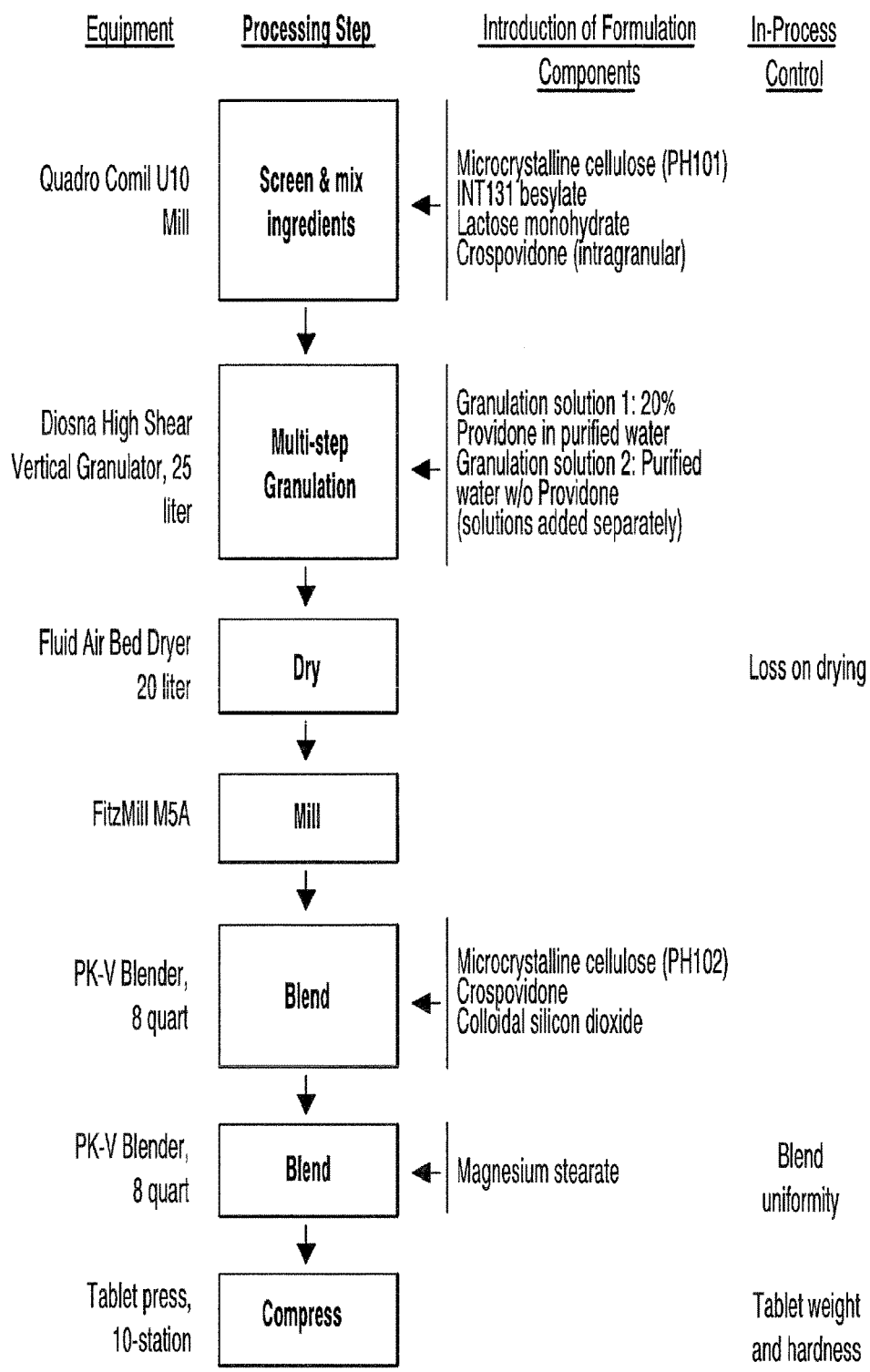
Fig. 7 Tablet Manufacturing Process

SOLID PHARMACEUTICAL COMPOSITIONS OF PPARγ MODULATOR

1. FIELD OF THE INVENTION

The present invention generally relates to solid pharmaceutical compositions of a selective peroxisome proliferator-activated receptor γ ("PPARγ") modulator; methods for preparing these compositions, and methods of their use for the treatment of various diseases and disorders.

2. BACKGROUND OF THE INVENTION

Peroxisome proliferator-activated receptor γ ("PPARγ") is one member of the nuclear receptor superfamily of ligand-activated transcription factors and has been shown to be expressed primarily in an adipose tissue-specific manner. Its expression is induced early during the course of differentiation of several preadipocyte cell lines. Additional research has now demonstrated that PPARγ plays a pivotal role in the adipogenic signaling cascade. PPARγ also regulates the ob/leptin gene which is involved in regulating energy homeostasis and adipocyte differentiation, which has been shown to be a critical step to be targeted for treating disorders such as obesity, diabetes and dyslipidemia.

In view of the clinical importance of PPARγ, compounds that modulate PPARγ function can be used for the development of new therapeutic agents. Potent modulators of PPARγ have been described, for example, in International Patent Publication No. WO 01/00579, and U.S. Pat. Nos. 6,200,995 B1, 6,583,157 B2, 6,653,332 B2, and 7,041,691 B1. One of these promising modulators, identified herein as compound 101 (or compound of formula (I)), is in clinical development for therapeutic treatment of Type 2 Diabetes. A suitable pharmaceutical composition or dosage form for this molecule is essential for its use in the prevention or treatment of disease. Pharmaceutical compositions that improve stability, increase bioavailability and improve ease of administration would be particularly useful. Dosage forms capable of facilitating administration of combination therapies are also desirable.

The free base and certain pharmaceutically acceptable salts of compound 101 are described in International Patent Publication No. WO01/00579, and U.S. Pat. Nos. 6,583,157 B2 and 7,041,691 B1. U.S. Pat. No. 7,223,761 B2 discloses that the benzenesulfonic acid (besylate) salt of compound 101, and polymorphs thereof, displays superior stability and hygroscopic properties when compared to other salts of compound 101. Despite the superior stability and hygroscopic properties of the besylate salt of compound 101, the besylate salt is sparingly soluble in aqueous solvents and in most organic solvents, which severely limits its effective concentration in a pharmaceutical preparation and can lead to decreased bioavailability upon administration.

U.S. Provisional Patent Application No. 61/102,658, discloses oral pharmaceutical preparations comprising liquid (oil-based) formulations of the besylate salt of compound 101 in a capsule. Despite the desirable solubility and bioavailability observed for the besylate salt of compound 101 in the oil-based formulation, the capsules are prone to leakage or precipitation of their contents over time. Leakage of the capsules' contents over time may result in loss of the active ingredient in the capsule, and may further result in a contamination of the contents of the capsule. Precipitation of the capsules' contents over time may result in loss of bioavailability.

A need therefore exists for a pharmaceutical composition of besylate and other salt and polymorphic forms of this class of PPARγ modulators which displays suitable bioavailability and shelf-life stability, and which is not susceptible to liquid capsule leakage over time. These and other unmet needs are addressed by this disclosure.

3. SUMMARY OF THE INVENTION

Embodiment (1)

In a first embodiment, the present invention provides an antidiabetic pharmaceutical composition, in solid form, suitable for oral administration to a subject, including but not limited to a human subject, which comprises a compound of formula (I):

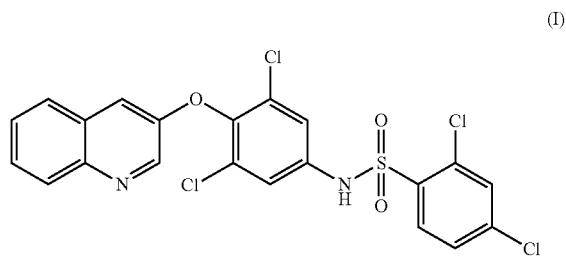 [SMILES: O=S(=O)(Nc1cc(Cl)c(Oc2cnc3ccccc3c2)c(Cl)c1)c1ccc(Cl)cc1Cl]

(I)

or a salt thereof, wherein the solid pharmaceutical composition, after administration to the subject, is capable of providing $AUC_{0\to\infty}$ (the area under the curve of a plot of plasma drug concentration versus time) for the compound (I) of at least, or about, 150-5000 ng*hr/mL. The compound of formula (I) is also referred to herein alternatively as compound 101.

In a further aspect of Embodiment (I), the solid pharmaceutical composition, after administration to a subject, is capable of providing $T_{max}$ for the compound of less than about 5.0 hours.

In a further aspect of Embodiment (1), the solid pharmaceutical composition, after administration to a subject, is capable of providing $T_{max}$ for the compound of formula (I) of less than about 4.0 hours.

In a further aspect of Embodiment (1), the compound of formula (I) is present as a salt thereof selected from the group consisting of benzenesulfonate salt, hydrochloride salt, hydrobromide salt, and p-toluenesulfonate salt.

In a further aspect of Embodiment (1), compound of formula (I) is present as the benzenesulfonate salt (alternatively referred to as the besylate salt), and the solid pharmaceutical composition, after administration to a subject, is capable of providing in the subject an $AUC_{0\to\infty}$ for the compound (I) of at least, or about, 150-5000 ng*hr/mL and $T_{max}$ for the compound of formula (I) of less than about 4.0 hours.

In a further aspect of Embodiment (1), the solid pharmaceutical composition in any of the foregoing aspects comprises at least one additional antidiabetic compound in addition to the compound of formula (I).

In a further aspect of Embodiment (1), the solid pharmaceutical composition in any of the foregoing aspects is in the form of a powder or tablet, including an encapsulated powder.

In a further aspect of Embodiment (1), the solid pharmaceutical composition in any of the foregoing aspects is provided as a unit dosage form.

In a further aspect of Embodiment (1), the solid pharmaceutical composition in any of the foregoing aspects is prepared by a process which comprises the steps of: (a) micronizing the compound of formula (I); and (b) performing a wet granulation of the micronized compound. One or more pharmaceutically acceptable excipients (or combinations thereof) may be included as intragranular material, included prior to conducting wet granulation; and/or such excipients may be added as extragranular material to the wet granulation product, i.e., added after the wet granulation product has been dried.

Embodiment (2)

The present invention is further directed to an antidiabetic pharmaceutical composition, in solid form, suitable for oral administration to a subject, including but not limited to a human subject, comprising a compound of formula (I):

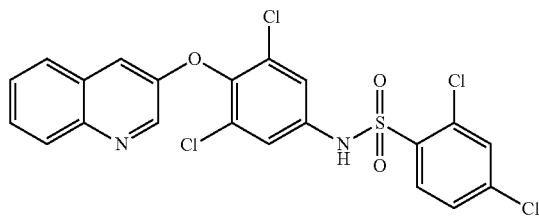

(I)

or a salt thereof, wherein the mean particle size of the compound of formula (I) is less than 150 microns.

In a further aspect of Embodiment (2), the mean particle size is less than 100 microns.

In a further aspect of Embodiment (2), the mean particle size is less than 50 microns.

In a preferred further aspect of Embodiment (2), the compound of formula (I) is provided in micronized form, and the mean particle size of the compound is, or is less than 20 microns.

In a particularly preferred aspect of Embodiment (2), the mean particle size is about 1 to 10 microns.

In a further aspect of Embodiment (2), the compound of formula (I) is present as a salt thereof selected from the group consisting of benzenesulfonate salt, hydrochloride salt, hydrobromide salt, and p-toluenesulfonate salt.

In a further aspect of Embodiment (2), the compound of formula (I) is present as the benzenesulfonate salt (alternatively referred to as the besylate salt).

In a further aspect of Embodiment (2), the compound of formula (I) is provided as the benzenesulfonate salt and is present in the pharmaceutical composition in an amount of about 0.1 to 10.0 mg.

In a further aspect of Embodiment (2), the solid pharmaceutical composition comprises one or more pharmaceutically acceptable excipients.

In a further aspect of Embodiment (2), the solid pharmaceutical composition comprises one or more excipients selected from the group consisting of fillers, diluents, superdisintegrants, binders, glidants, lubricants, and combinations thereof.

In a further aspect of Embodiment (2), the solid pharmaceutical composition comprises one or more pharmaceutically acceptable excipients selected from the group consisting of lactose monohydrate, microcrystalline cellulose, crospovidone, povidone, colloidal silicon dioxide, magnesium stearate, and combinations thereof.

In a further aspect of Embodiment (2), the solid pharmaceutical composition is provided as a unit dosage form, which upon oral administration to a human subject provides in the subject an $AUC_{0 \to \infty}$ for the compound (1) of at least, or about, 150-5000 ng*hr/mL, and a $T_{max}$ for the compound that is, or is less than, 4.0 hours.

In a further aspect of Embodiment (2), the composition is in the form of a loose powder, a tablet, a caplet, or encapsulated powder, and comprises:
(1) the compound of formula (I) provided as the besylate salt thereof and constituting about 0.6 to 7.0 percent of the composition;
(2) lactose monohydrate constituting about 25% to about 35% of the composition;
(3) crospovidone constituting about 4% to about 5% of the composition;
(4) microcrystalline cellulose constituting about 50% to about 60% of the composition;
(5) povidone constituting about 1% to about 3% of the composition;
(6) optionally, colloidal silicon dioxide constituting up to about 0.7% of the composition; and
(7) magnesium stearate constituting about 0.25% to about 1.5% of the composition.
wherein all percentages are percentages by weight.

In a further aspect of Embodiment (2), the solid pharmaceutical composition has a dissolution rate such that at least 75% of the compound of formula (I) is dissolved within 45 minutes, based on dissolution testing carried out using USP Type 2 apparatus (paddle) in an aqueous medium containing 0.5% SDS at pH 1.5 (with HCl), at a mixing speed of 50 rpm (900 mL at 37° C.).

In a particularly preferred aspect of Embodiment (2), the solid pharmaceutical composition according to any of the previous aspects of this Embodiment is prepared by a process which comprises the steps of (a) micronizing the compound of formula (I); and (b) performing wet granulation of the compound of formula (I) in combination with one or more pharmaceutically acceptable excipients. It was surprising that wet granulation, preferably in conjunction with use of micronized active ingredient milled to an average size of less than 150 microns, and most preferably a size of 1 to about 10 microns, is able to provide a uniform and stable pharmaceutical composition that has excellent dissolution and bioavailability, comparable to an oil-based liquid-filled capsule, as disclosed in U.S. Provisional Patent Application No. 61/102,658, while avoiding the problems of capsule integrity often associated with liquid-filled capsules.

Embodiment (3)

In a third embodiment, the invention is directed to a method of making a pharmaceutical composition, in solid form, comprising a compound of formula (I):

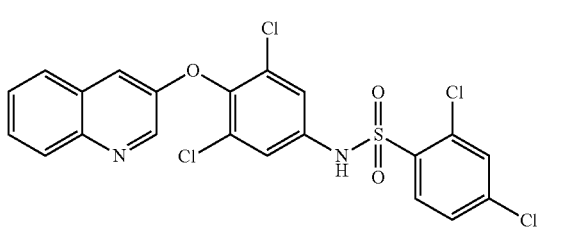

(I)

or a salt thereof, wherein said solid pharmaceutical composition is made by wet granulation.

In a further aspect of Embodiment (3), the method comprises the steps of:
  (a) screening and mixing micronized particles of the compound of formula (I) with one or more excipients to form a powder blend;
  (b) adding a granulation solution to the intragranular material obtained in (a), and mixing the solution and powder blend to form wet granules:
  (c) drying the wet granules obtained in (b) to form dry granules;
  (d) milling the dry granules obtained in (c);
  (e) blending the milled dry granules obtained in (d) with extragranular material comprised of one or more excipients to form a blend constituting a final dosage formulation of the solid pharmaceutical composition; and
  (f) optionally, compressing the blend obtained in (e) into a unit dosage form.

In a further aspect of Embodiment (3), the excipients are selected from the group consisting of diluents, fillers, superdisintegrants, binders, glidants, lubricants, and combinations thereof.

In a further aspect of Embodiment (3), excipients are selected from the group consisting of microcrystalline cellulose, lactose monohydrate, crospovidone, povidone, colloidal silicon dioxide, and magnesium stearate; and the process includes steps (e) and (f).

In a particularly preferred aspect of Embodiment (3), the method comprises the additional step of (b)(i) adding a granulating solution to the wet granules obtained in step (b) to form wet granules of different composition than those obtained in step (b); wherein the granulating solution added in step (b)(i) is the same composition as, or is different in composition from, the granulating solution added in step (b). This is a preferred method of granulation as it is unexpectedly found to result in compositions having higher potency, as will be demonstrated in the examples.

In a further aspect of Embodiment (3), employing step (b)(i) of the preceding paragraph, the method of this embodiment is carried out such that the granulating solution added in step (b) comprises at least about 15% and preferably at least about 20% w/w povidone in granulating water, and the granulating solution added in step (b)(i) is water essentially free of povidone, or water containing povidone but in an amount less than the amount thereof provided in the granulating solution of step (b).

Embodiment (4)

A fourth embodiment of the invention is directed to a pharmaceutical composition, in solid form, suitable for unit dosage administration to a subject, preferably a human, in powdered, tableted or encapsulated form, comprising a pharmaceutical composition prepared by any of the wet granulation techniques described for Embodiment (3).

Embodiment (5)

In a fifth embodiment, the invention is directed to a method of preparing a wet granulation product suitable as a precursor for manufacture of a solid form antidiabetic pharmaceutical preparation, said wet granulation method comprising the steps of:
  (a) mixing micronized particles of the compound of formula (I):

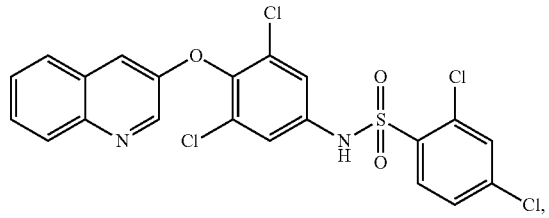

or a salt thereof, with one or more excipients, to form an intragranular material;
  (b) adding a granulation solution to the intragranular material obtained in (a), and granulating the solution and intragranular material to form wet granules;

In a further aspect of either the methods of Embodiment (4), or the methods of Embodiment (3), the compound of formula (I) is provided as the besylate salt thereof, and the micronized particles of the compound of formula (I) have a mean particle size of less than about 50 microns, and preferably about, or less than 20 microns.

In a further aspect of either the methods of Embodiment (5), the method comprises the additional step of (b)(i) adding a granulating solution to the wet granules obtained in step (b) to form wet granules of different composition than those obtained in step (b); wherein the granulating solution added in step (b)(i) is the same composition as, or is different in composition from, the granulating solution added in step (b).

In a further aspect of Embodiment (5), employing step (b)(i) of the preceding paragraph, the method of this embodiment is carried out such that the granulating solution added in step (b) comprises at least about 15% and preferably at least about 20% w/w povidone in granulating water, and the granulating solution added in step (b)(i) is water essentially free of povidone, or water containing povidone but in an amount less than the amount thereof provided in the granulating solution of step (b).

Embodiment (6)

A sixth embodiment of the invention is directed to a pharmaceutical precursor composition obtained from the wet granulation performed using any of the method aspects described for Embodiment (5), where the precursor is suitable for use in manufacturing a solid unit oral dosage form of the compound of formula (I).

In a particularly preferred aspect of Embodiment (6), the precursor prepared using wet granulation comprises:
  (a) about 0.5 to about 7.0% of the besylate salt of compound of formula (I);
  (b) about 25% to 45% lactose monohydrate;
  (c) about 25% to 45% microcrystalline cellulose;
  (d) about 2% to 4% povidone;
  (e) about 15% to about 24% water;
wherein all percentages are weight percentages.

In a further aspect of Embodiment (6), the ratio of intragranular microcrystalline cellulose to intragranular lactose monohydrate is from about 1.8:1 to about 0.67:1, and most preferably about 1.5:1.

In a further aspect of Embodiment (6), the water (e) used for granulation has been removed, resulting in dried granules.

In each of the Embodiments (1), (2), (4) and (6), the composition comprising formula (I) may further comprise an antidiabetic compound in addition to the compound of formula (I). If a further antidiabetic compound is added to the precursor of embodiment 6 as additional active in component (a) thereof, the amount of excipient(s) used in the precursor composition may be adjusted in a known manner to accommodate the additional active ingredient.

In each of the composition Embodiments (1), (2), (4) and (6), the solid pharmaceutical composition, when provided as a tablet containing 0.5 to 10 mg of the compound of formula (I), has a dissolution rate such that at least 75% of the compound of formula (I) is dissolved within 45 minutes, based on dissolution testing carried out using USP Type 2 apparatus (paddle), in an aqueous medium (900 mL, 37° C.) containing 0.5% SDS at pH 1.5 (with HCl), at a mixing speed of 50 rpm.

Embodiment (7)

A seventh embodiment of the invention is directed to a method of treating, preventing or ameliorating a PPARγ-mediated condition or disorder in a subject, the method comprising administering to the subject a therapeutically effective amount of the solid pharmaceutical composition as described in the preceding embodiments. The PPARγ-mediated condition or disorder includes metabolic disorders or inflammatory disorders. Metabolic disorders include diabetes, obesity, hypercholesterolemia, hyperlipidemia, dyslipidemia, hypertriglyceridemia, hyperglycemia, insulin resistance and hyperinsulinemia. In preferred aspects of Embodiment (7), the treated metabolic disorder is Type 2 Diabetes; and the treated inflammatory conditions are rheumatoid arthritis and atherosclerosis. The intended treatment uses encompass human as well as veterinary applications.

4. DESCRIPTION OF FIGURES

FIG. 1. Dissolution data for pharmaceutical compositions of the present invention comprising the besylate salt of Compound 101, prepared via micronization and wet granulation.

Figure 2:
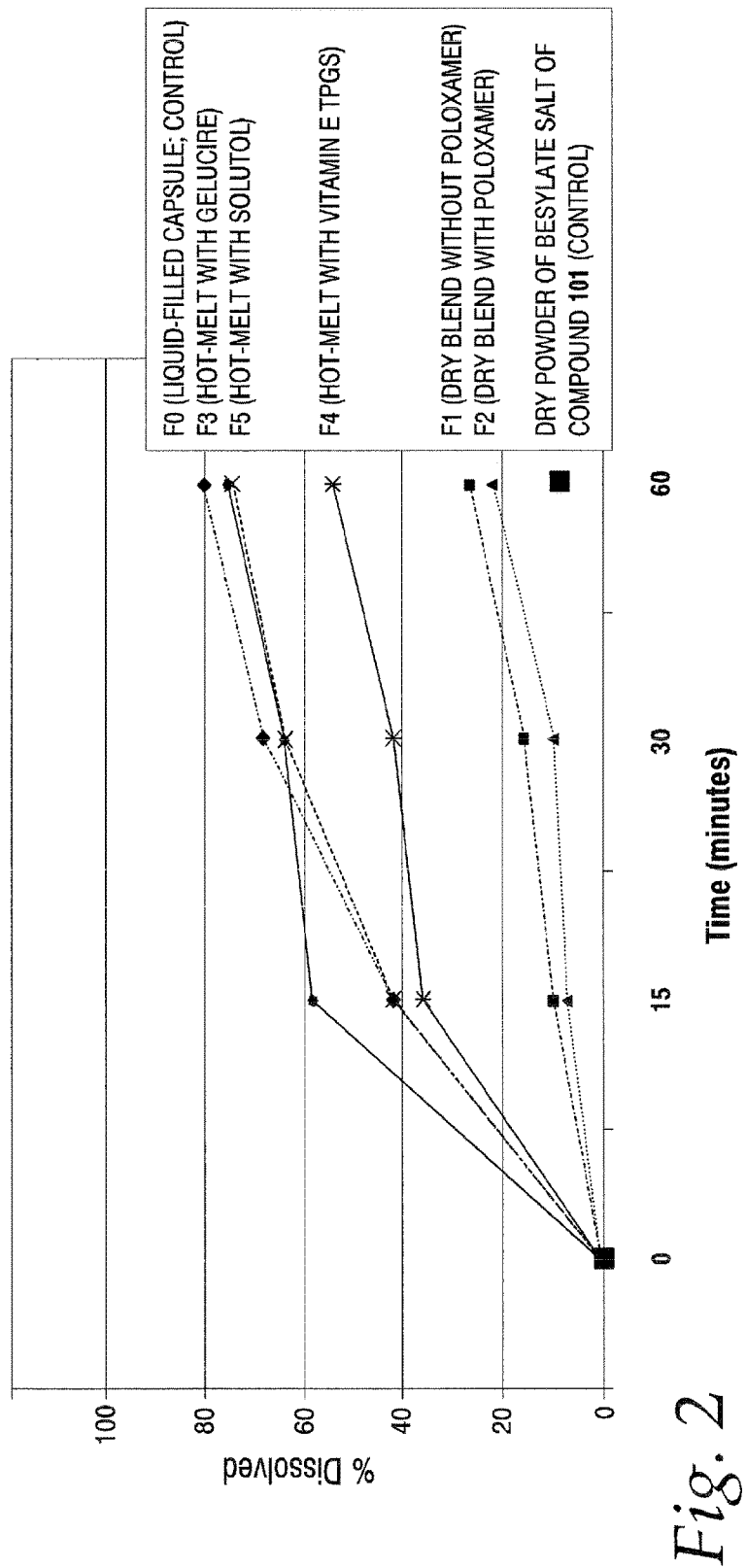

FIG. 2. Comparative: Dissolution data for dry blend and hot-melt capsule formulations of the besylate salt of Compound 101.

Figure 3:
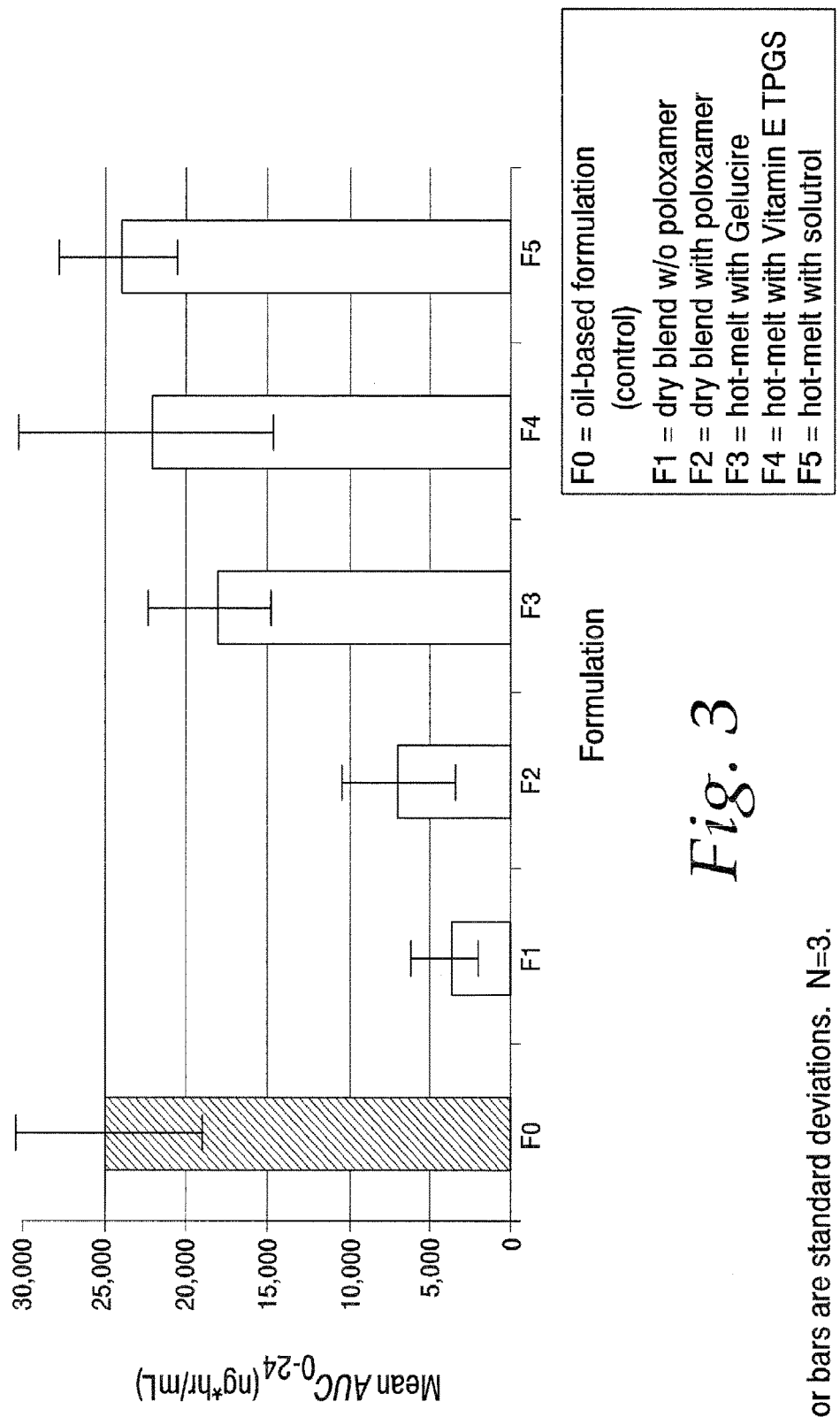

FIG. 3. Comparative: Bioavailability (AUC) of dry blend and hot-melt capsule formulations of the besylate salt of Compound 101.

Figure 4:
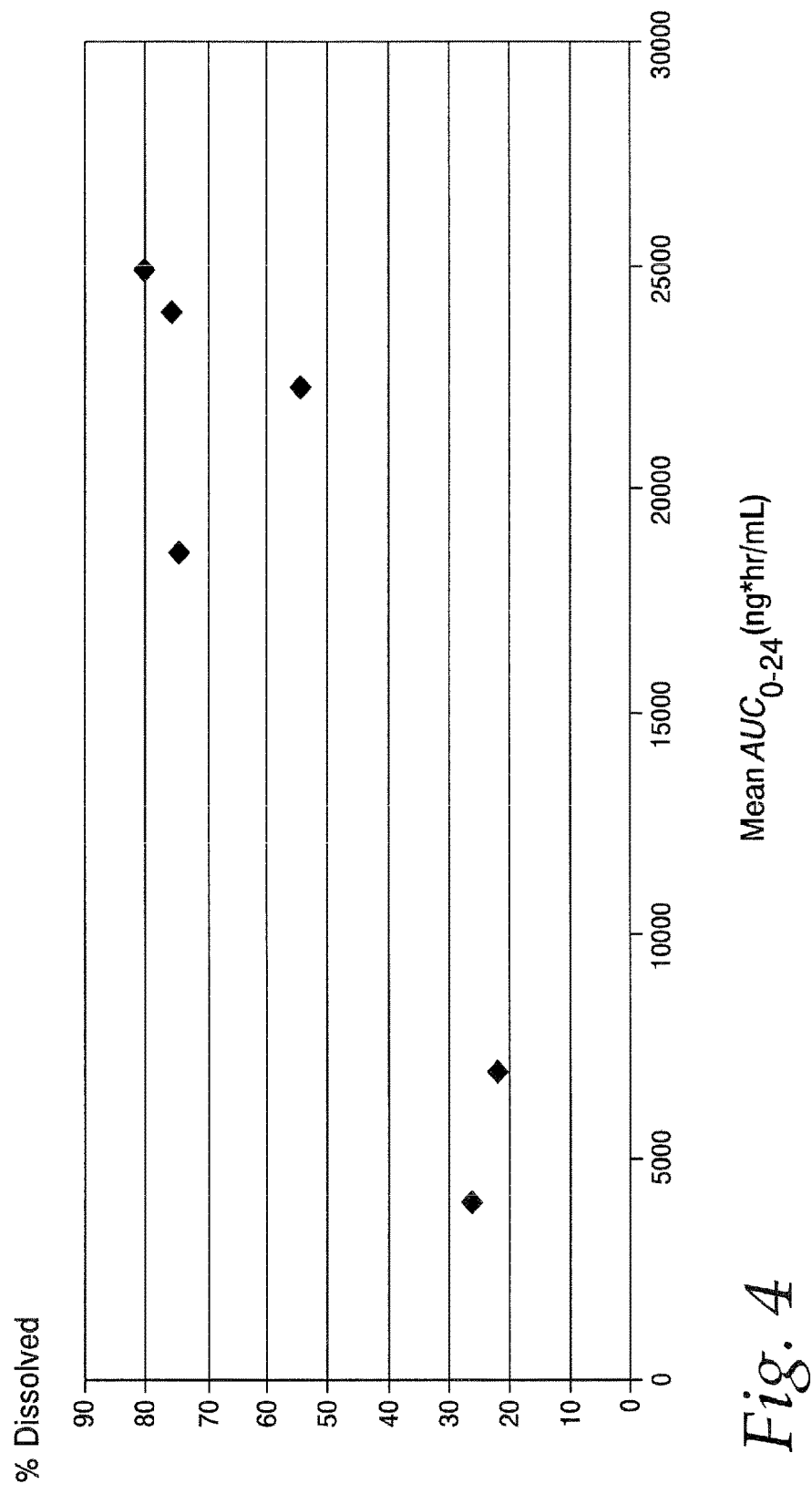

FIG. 4. Correlation between bioavailability (AUC) and dissolution of the dry blend and hot-melt capsule formulations of the besylate salt of Compound 101.

Figure 5:
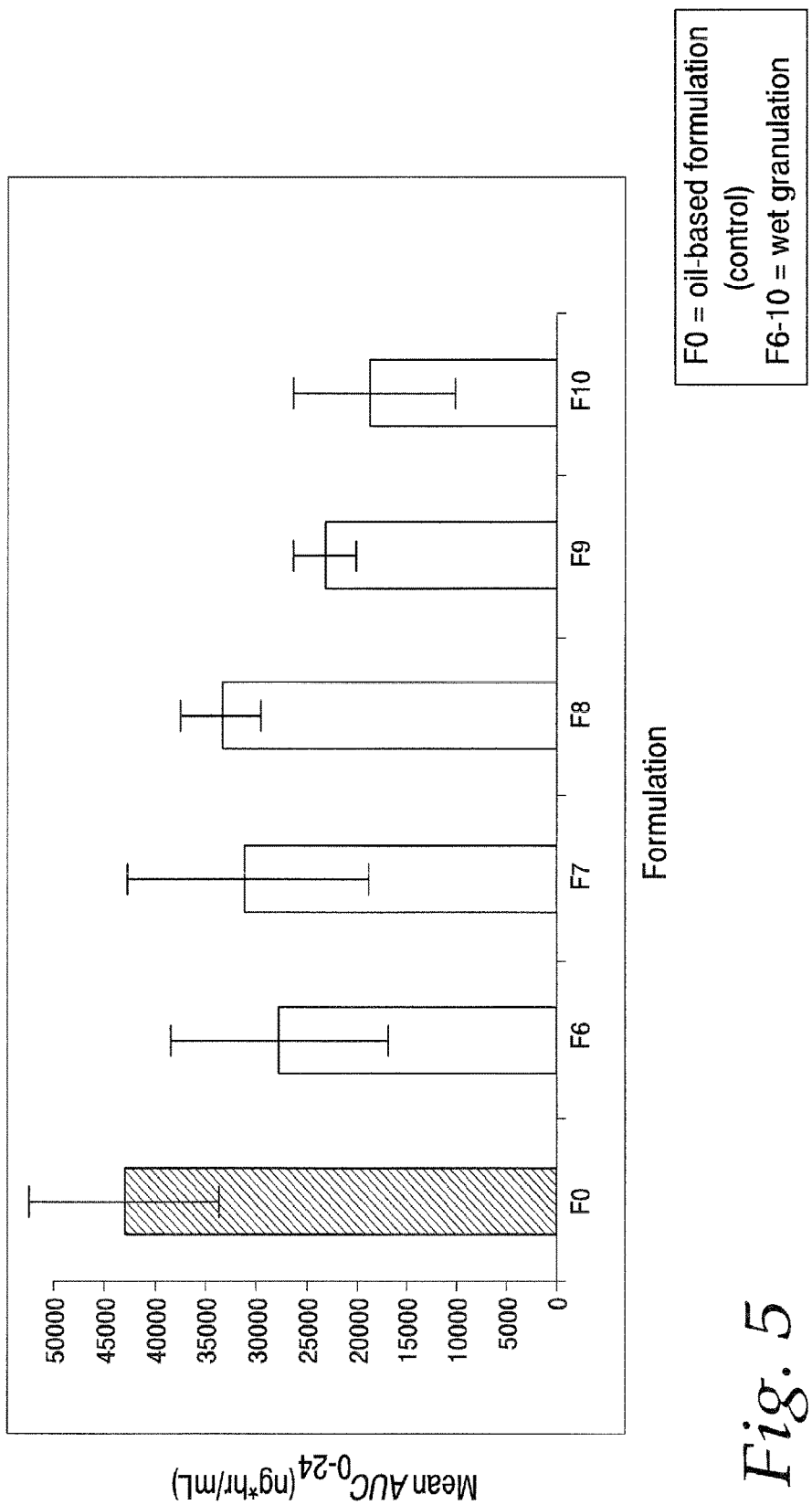

FIG. 5. Bioavailability (AUC) data for pharmaceutical compositions of the present invention comprising the besylate salt of Compound 101, prepared via micronization and wet granulation.

Figure 6:
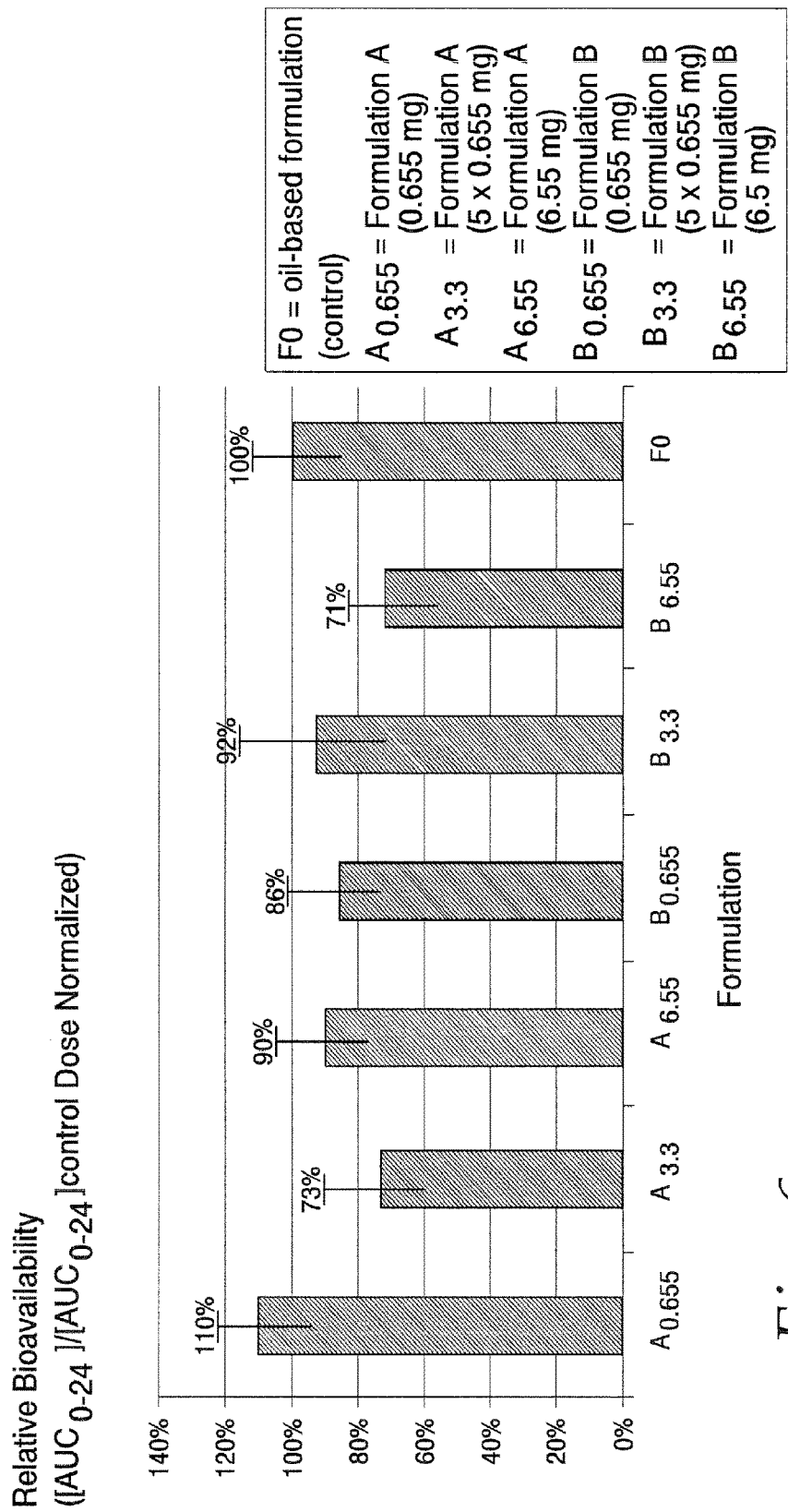

FIG. 6. Relative bioavailability (AUC) and $T_{max}$ of Formulations A and B of the besylate salt of Compound 101.

FIG. 7. Exemplary manufacturing process for a tablet of the besylate salt of Compound 101.

(Note that the bioavailability data presented in FIGS. 3-6 was obtained in monkeys)

5. DETAILED DESCRIPTION 5.1 Definitions

The term "composition" as used herein is intended to encompass a product comprising the specified ingredients (and in the specified amounts, if indicated), as well as any product which results, directly or indirectly, from combination of the specified ingredients in the specified amounts. By "pharmaceutically acceptable" it is meant the diluent, excipient or carrier must be compatible with the other ingredients of the formulation and not deleterious to the recipient thereof.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

The term "solid forms" and related terms used herein, unless otherwise specified, refers to crystalline forms and amorphous forms comprising compound 101 and its various salt forms.

The term "micronized," "micronizing" or "micronization" means the process of reducing the average diameter of a solid material's particles.

The term "wet granulation" refers to the product of a wet granulation process, which typically involves the following successive steps: (i) mixing an active ingredient with at least one excipient, binder or diluent to form a powder blend; (ii) adding a granulating solution which may contain one or more excipients in a solvent to obtain, by high speed mixing, a wet granulation; (iii) drying, milling and/or blending the wet granulation with additional amounts of least one excipient to obtain a blend; and (iv) optionally compressing the dried granulation or blend obtained in (iii) into a unit dosage form, for example, a tablet. The excipients added after wet granulation can be of the same or different quality/grade of the same excipients used before or during the wet granulation process. Preferably, a lubricant is added to the bulk blend before compression. See, for example, Ansel et al., *Pharmaceutical Dosage Forms and Drug Delivery Systems*, 6$^{th}$ ed., Williams & Wilkins, Baltimore Md. (1995), pp. 194-204; the content of which is incorporated by reference in its entirety.

The term "crystalline" and related terms used herein, when used to describe a substance, component or product, means that the substance, component or product is crystalline as determined by X-ray diffraction. See, for example, *Remington's Pharmaceutical Sciences*, 18$^{th}$ ed., Mack Publishing, Easton Pa., p. 173 (1990); *The United States Pharmacopeia*, 23$^{rd}$ ed., pp. 1843-1844 (1995); the contents of which are hereby incorporated by reference in their entireties.

The term "crystalline forms" and related terms herein refers to the various crystalline modifications of a given substance, including, but not limited to, polymorphs, solvates, hydrates, co-crystals and other molecular complexes, as well as salts, solvates of salts, hydrates of salts, other molecular complexes of salts, and polymorphs thereof.

The term "pharmaceutically acceptable salts" is meant to include salts of active compounds which are prepared with relatively nontoxic acids. Acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic; propionic; isobutyric; maleic; malonic; benzoic; succinic; suberic; fumaric; mandelic; phthalic; benzenesulfonic; toluenesulfonic, including p-toluenesulfonic, m-toluenesulfonic, and o-toluenesulfonic; citric; tartaric; methanesulfonic; and the like. Also included are salts of amino acids such as arginate and the like, and salts of organic acids like glucuronic or galactunoric acids and the like (see, for example, Berge et al. J. Pharm. Sci. 66:1-19 (1977)).

As used herein, a salt or polymorph that is "pure," i.e., substantially free of other polymorphs, contains less than about 10% of one or more other polymorphs, preferably less than about 5% of one or more other polymorphs, more preferably less than about 3% of one or more other polymorphs, most preferably less than about 1% of one or more other polymorphs.

The term, "amorphous form," as used herein, refers to a noncrystalline form of a substance.

The terms, "polymorphs" and "polymorphic forms" and related terms herein refer to crystal forms of a molecule. Different polymorphs may have different physical properties such as, for example, melting temperatures, heats of fusion, solubilities, dissolution rates and/or vibrational spectra as a result of the arrangement or conformation of the molecules in the crystal lattice. The differences in physical properties exhibited by polymorphs affect pharmaceutical parameters such as storage stability, compressibility and density (important in formulation and product manufacturing), and dissolution rates (an important factor in bioavailability). Polymorphs of a molecule can be obtained by a number of methods, as known in the art. Such methods include, but are not limited to, melt recrystallization, melt cooling, solvent recrystallization, desolvation, rapid evaporation, rapid cooling, slow cooling, vapor diffusion and sublimation.

Techniques for characterizing polymorphs include, but are not limited to, differential scanning calorimetry (DSC), X-ray powder diffractometry (XRPD), single crystal X-ray diffractometry, vibrational spectroscopy, e.g., IR and Raman spectroscopy, solid state NMR, hot stage optical microscopy, scanning electron microscopy (SEM), electron crystallography and quantitative analysis, particle size analysis (PSA), surface area analysis, solubility studies and dissolution studies.

The term, "solvate," as used herein, refers to a crystal form of a substance which contains solvent. The term "hydrate" refers to a solvate wherein the solvent is water.

The term, "desolvated solvate," as used herein, refers to a crystal form of a substance which can only be made by removing the solvent from a solvate.

The term "alkyl," as used herein, refers to monovalent saturated aliphatic hydrocarbyl groups particularly having up to about 11 carbon atoms, more particularly as a lower alkyl, from 1 to 8 carbon atoms and still more particularly, from 1 to 6 carbon atoms. The hydrocarbon chain may be either straight-chained or branched. This term is exemplified by groups such as methyl, ethyl, n-propyl, isopropyl, n-butyl, iso-butyl, tert-butyl, n-hexyl, n-octyl, tert-octyl and the like. The term "lower alkyl" refers to alkyl groups having 1 to 6 carbon atoms. The term "alkyl" also includes "cycloalkyl" as defined below.

The term "heteroalkyl," by itself or in combination with another term, means, unless otherwise stated, a stable straight or branched chain, or cyclic hydrocarbon radical, or combinations thereof, consisting of the stated number of carbon atoms and from one to three heteroatoms selected from the group consisting of O, N, Si and S, and wherein the nitrogen and sulfur atoms may optionally be oxidized and the nitrogen heteroatom may optionally be quaternized. The heteroatom(s) O, N and S may be placed at any interior position of the heteroalkyl group. The heteroatom Si may be placed at any position of the heteroalkyl group, including the position at which the alkyl group is attached to the remainder of the molecule. Examples include —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$—S(O)—$CH_3$, —$CH_2$—$CH_2$—S(O)$_2$—$CH_3$, —CH=CH—O—$CH_3$, —Si($CH_3$)$_3$, —$CH_2$—CH=N—O$CH_3$, and —CH=CH—N($CH_3$)—$CH_3$. Up to two heteroatoms may be consecutive, such as, for example, —$CH_2$—NH—O$CH_3$ and —$CH_2$—O—Si($CH_3$)$_3$. Also included in the term "heteroalkyl" are those radicals described in more detail below as "heteroalkylene" and "heterocycloalkyl."

"Aryl" refers to a monovalent aromatic hydrocarbon group derived by the removal of one hydrogen atom from a single carbon atom of a parent aromatic ring system. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexylene, as-indacene, s-indacene, indene, indene, naphthalene, octacene, octaphene, octacene, ovalene, penta-2,4-diene, pentacene, pentalene, pentaphene, perylene, phenalene, phenanthrene, picene, pleiadene, pyrene, pyranthrene, rubicene, triphenylene, trinaphthalene and the like. Particularly, an aryl group comprises from 6 to 14 carbon atoms.

The term "excipient" refers to an inactive ingredient of the pharmaceutical compositions of the invention. It includes, but is not limited to, solvents, wetting agents, diluents, superdisintegrants, binders, glidants, and lubricants.

The terms "treat", "treating" or "treatment", as used herein, refer to the reduction or amelioration of the progression, severity, and/or duration of a disorder or the eradication, reduction or amelioration of symptoms of a disorder, or the delay of the recurrence or onset of a disorder or one or more symptoms thereof in a subject that results from the administration of one or more compound.

The term "therapeutically effective amount" refers to the amount of the subject salt or polymorph that will elicit the biological or medical response of a tissue, system, animal or human that is being sought by the researcher, veterinarian, medical doctor or other clinician or that is sufficient to prevent development of or alleviate to some extent one or more of the symptoms of the disease being treated.

The term "subject" is defined herein to include animals such as mammals, including, but not limited to, primates (e.g., humans), cows, sheep, goats, horses, dogs, cats, rabbits, rats, mice and the like. In preferred embodiments, the subject is a human.

As used herein, "diabetes" refers to type I Diabetes (juvenile diabetes), Type 2 Diabetes mellitus (non-insulin-dependent diabetes mellitus or T2DM), and pre-diabetes. Pre-diabetes is defined as a condition in which a fasting plasma glucose test and/or an oral glucose tolerance test provide readings that are elevated, but not considered diabetic.

The term "obesity" as used herein is a condition in which there is an excess of body fat. In certain embodiments, obesity is defined based on the Body Mass Index (BMI), which is calculated as body weight per height in meters squared kg/m$^2$. In some embodiments, an "obese subject" can be an otherwise healthy subject with a Body Mass Index (BMI) greater than or equal to 30 kg/m$^2$ or a subject with at least one co-morbidity with a BMI greater than or equal to 27 kg/m². In some embodiments, a "subject at risk of obesity" can be an otherwise healthy subject with a BMI of 25 kg/m² to less than 30 kg/m² or a subject with at least one co-morbidity with a BMI of 25 kg/m² to less than 27 kg/m².

The term "metabolic syndrome" as used herein is as defined by the Adult Treatment Panel III (ATP III; National Institutes of Health: Third Report of the National Cholesterol Education Program Expert Panel on Detection, Evaluation, and Treatment of High Blood Cholesterol in Adults (Adult Treatment Panel III), Executive Summary; Bethesda, Md., National Institutes of Health, National Heart, Lung and Blood Institute, 2001 (NIH pub. No 01-3670). Briefly, metabolic syndrome occurs when a subject meets three or more of five criteria related to obesity, hypertriglyceridemia, low HDL cholesterol, high blood pressure, and high fasting glucose.

As used herein, the term "PPARγ-mediated condition or disorder" or "PPARγ-mediated condition or disease," refers to a condition, disorder or disease in which modulation of PPARγ results in mitigation of the underlying condition, disorder or disease (e.g., a PPARγ modulator results in some improvement in patient well-being in at least some patients). Exemplary PPARγ-mediated conditions and disorders include, but are not limited to, metabolic disorders, e.g., diabetes, Type 2 Diabetes, obesity, hyperglycemia, insulin resistance, hyperinsulinemia, hypercholesterolemia, hypertension, hyperlipoproteinemia, hyperlipidemia, hypertriglyceridemia and dyslipidemia, and inflammatory conditions, e.g., rheumatoid arthritis and atherosclerosis.

The term "selective modulator of PPARγ" as used herein is defined as any natural or synthetic substance capable of binding to a PPARγ nuclear receptor in such a manner that the substance activates the receptor's ability to cause one or more desired biological effects, without also activating (or with substantially reduced activation of) the receptor's ability to cause one or more undesired biological effects. For example, selective modulators of PPARγ suitable for administration to a diabetic patient in the combinations of the present invention include compounds such as Compound 101 that either naturally (or by design, in the case of compound 101) are capable of interacting with the PPARγ binding pocket in a manner that results in the same or substantially the same insulin sensitizing effects attainable from so-called "full agonists" of PPARγ such as rosiglitazone (Avandia®) and pioglitazone (Actos®), but without, or with substantial mitigation of, the known harmful side effects associated with such full agonists, including, for example, their tendency to promote weight gain, fluid retention, and bone fracture. The term "selective modulator of PPARγ" should thus be understood to exclude substances such as the full agonists of PPAR that are generally understood by persons of ordinary skill in the art as being able to activate substantially the full spectrum of PPARγ effects, while having little if any ability to differentially activate only the beneficial effects of the receptor and not its harmful effects. A specific example of a class of full PPARγ agonists excluded from the present definition of "selective modulator of PPAR" is the thiazolidinedione (TZD) class of PPARγ full agonists. One of the key benefits of a selective PPARγ modulator is that, unlike a full or non-selective PPARγ agonists, administering increasing dosages of a selective modulator of PPARγ to a patient with diabetes can result in an increase in therapeutic benefits over the selected dose range, with little if any concomitant increase in harmful side effects. This separation in the dose response curves for beneficial versus harmful effects allows a broad therapeutic window for administration of a selective modulator of PPARγ to a diabetic patient. Selective modulators of PPARγ (also called SPPARM's) are discussed in "Higgins L S, Montzoros C S, "The development of INT131 as a Selective PPARγ Modulator: Approach to a Safer Insulin Sensitizer," PPAR Research Volume 2008; Article ID 936906; and Zhang F, Lavan B E, Gregoire F M. "Selective Modulators of PPARγ Activity: Molecular Aspects Related to Obesity and Side-Effects," PPAR Research Volume 2007 Article ID 32696; and Fujimora T, Kimura C, Oe T, Takata Y, Sakuma H, Aramori, I Mutoh S. "A Selective Peroxisome Proliferator-Activated Receptor γ Modulator with Distinct Fat Cell Regulation Properties,"Journal of Pharmacology and Experimental Therapeutics 2006 Vol 318, No 2 pages 863-871. These publications are incorporated by reference herein in their entirety. To the extent references cited within these publications disclose selective PPARγ modulators, as defined herein, such cited references are further understood to be incorporated by reference herein in their entirety.

As used herein, the term "about" or "approximately" means an acceptable error for a particular value as determined by one of ordinary skill in the art, which depends in part on how the value is measured or determined. In certain embodiments, the term "about" or "approximately" means within 1, 2, 3, or 4 standard deviations. In certain embodiments, the term "about" or "approximately" means within 50%, 20%, 15%, 10%, 9%, 8%, 7%, 6%, 5%, 4%, 3%, 2%, 1%, 0.5%, or 0.05% of a given value or range.

The term, "AUC," as used herein, refers to the area under the curve of a plot of plasma drug concentration versus time.

The term, "$T_{max}$," as used herein, refers to the time after administration of a drug when the maximum plasma concentration is reached.

The term "intragranular" is intended to refer to ingredients of the pharmaceutical composition of the present invention that are combined in a wet granulation process using a liquid granulating solution to produce wet granules that contain the granulated ingredients.

The term "extragranular" is intended to refer to ingredients of the pharmaceutical composition of the present invention that are combined (e.g., dry blended) with a wet granulation product, after the latter wet granulation product has been converted from wet granules to dry powder.

5.2 Detailed Description of Compositions and Methods

The present invention provides solid pharmaceutical compositions that are suitable for oral delivery of selective PPARγ modulators, wherein the compositions comprise a compound of formula (I) (also referred to herein as compound 101):

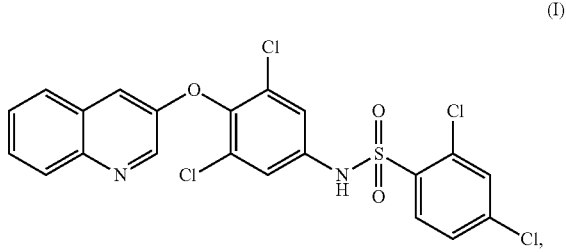 [SMILES: O=S(=O)(Nc1cc(Cl)c(Oc2cnc3ccccc3c2)c(Cl)c1)c1ccc(Cl)cc1Cl]

(I)

or a salt thereof, and at least one pharmaceutically acceptable excipient, wherein the composition, when orally administered to a subject, exhibits excellent bioavailability affording suitability for use in preparing unit dosage forms for oral administration, in solid form, to subjects requiring treatment for PPARγ mediated conditions. In its method aspects, the invention further provides methods for manufacturing the compositions that can achieve the desired bioavailability and stability in the oral unit dosage form of the pharmaceutical composition comprising the compound of formula (I).

The methods of the invention encompass micronization of the compound of formula (I) to a mean particle size of less than 150 microns, and preferably about or less than 20 microns, followed by performance of wet granulation of the resultant micronized compound in combination with one or more pharmaceutically acceptable excipients. Such excipients can be (a) included as intragranular ingredients prior to or during wet granulation, so as to be subject to the wet granulation process; and/or (b) added as extragranular excipients to (e.g., dry blended with) an already prepared and dried wet granulation mixture.

A further feature of the invention is the discovery that formulations of compound (I) prepared by dry blending and hot melt processes did not result in pharmaceutical compositions displaying commercially acceptable combinations of the attributes of oral bioavailability, shelf stability (degradation or loss of potency under accelerated storage conditions) and product uniformity, all of which were successfully achieved in the compositions, and via the methods, of the present invention. Moreover, while the liquid-filled capsules generally offer comparable attributes of bioavailability and solubility, the formulations disclosed herein alleviate the problems associated with potential leakage or precipitation of the oil-based, liquid-filled capsules over time.

In accordance with a particularly preferred practice of the invention, the compound of formula (I), provided as the besylate salt, is micronized prior to wet granulation to result in particles of the compound having a mean particle size of about 1 to 10 microns. The besylate salt of compound (I) is provided in amounts sufficient to constitute about 0.1 to about 10 mg of the pharmaceutical composition, and preferably about 0.5 to 5 mg in a final unit dosage solid tablet or encapsulated powder form. In a preferred method, the composition is prepared by conducting wet granulation of the micronized besylate salt with one or more pharmaceutically acceptable excipients included as intragranular materials. In a particularly preferred practice of the wet granulation process, it is surprisingly found that superior potency (greater than 95%) of compound (I) can be achieved in the composition if the wet granulation is conducted in a multi-step fashion involving a first addition of binder (e.g., povidone) and granulation water at a higher concentration of binder than ultimately desired; followed by an additional granulation step using only water or water and a lesser concentration of binder. Using the preferred methods of preparation of the present invention, the compound of formula (I) exhibits a dissolution rate such that at least 75% of the compound is dissolved after 45 minutes. Following administration as a unit dosage form to a subject requiring treatment for a PPARγ mediated condition, the pharmaceutical composition is capable of providing in the subject an $AUC_{0 \to \infty}$ (the area under the curve of a plot of plasma drug concentration versus time) for the compound (I) of at least, or about, 150-5000 ng*hr/mL, and $T_{max}$ equal to or less than 4.0 hours.

The invention is further directed to a pre-cursor composition made by wet granulation, which can be used as an intermediate material suitable for providing a convenient uniform blend of the compound of formula (I) with other medicinal ingredients, such as additional anti-diabetic agents, prior to final preparation of a unit dosage formulation containing the combination. The precursor may be prepared by combining micronized compound of formula (I) with one or more additional therapeutic agents prior to subjecting the combined ingredients to wet granulation. Alternatively, wet granules may be initially prepared with micronized compound (I) as the only active therapeutic agent, whereupon, following preparation of a wet granulation material, one or more additional anti-diabetic agents may be added to the initial granulation product either before or after that product is dried. The amount of excipient(s) in either the precursor composition, or the final solid pharmaceutical composition, may be adjusted in a known manner to accommodate the presence of additional anti-diabetic ingredients.

5.2.1.1 Compound 101

A selective PPARγ modulator most suitable for use in the pharmaceutical compositions of the present invention is the selective PPAR-γ modulator (2,4-Dichloro-N-[3,5-dichloro-4-(quinolin-3-yloxy)-phenyl]-benzenesulfonamide benzenesulfonate salt), or compound 101 having the general formula (I), or a pharmaceutically acceptable salt, hydrate or polymorph thereof:

(101)

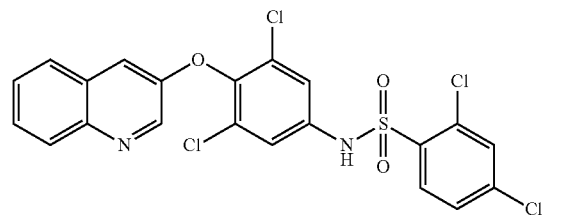

(I)

The above selective PPARγ modulator of compound 101 is disclosed, for example, in international Patent Publication No. WO 01/00579 (corresponding to U.S. Pat. No. 7,041,691), U.S. Pat. No. 6,200,995, U.S. Pat. No. 6,583,157, U.S. Pat. No. 6,653,332, the contents of which are incorporated by reference in their entireties.

5.2.1.2 Salts of Compound 101

The pharmaceutical compositions of the invention may include pharmaceutically acceptable salts of compound 101. These salts include, but are not limited to, HCl, HBr, tosylate, and besylate salts of compound 101.

In preferred embodiments, besylate salts of compound 101 are used within the methods and compositions. A preferred besylate salt of compound 101 is provided by formula (I):

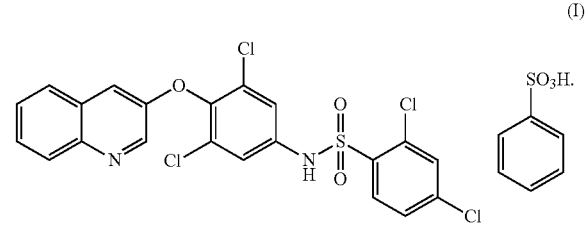

(I)

Each salt provided herein can be made from a preparation of compound 101, which can be synthesized or obtained according to any method apparent to those of skill in the art. In certain embodiments, compound 101 is prepared according to the methods described in U.S. Pat. No. 6,583,157 B2 and U.S. Pat. No. 7,223,761 B2, the contents of which are hereby incorporated by reference in their entireties.

5.2.1.3 Polymorphs of Compound 101

Also useful within the compositions and methods are polymorphs of compound 101. In certain embodiments, the polymorphs are polymorphs of the besylate salt of compound 101 described above. In certain embodiments, the polymorphs can be pure polymorphs of the besylate salt of compound 101. For example, a polymorph can be a pure Form I polymorph or a pure Form II polymorph of the besylate salt of compound 101.

The polymorphs of the HCl, HBr, tosylate, and besylate salts of compound 101 have been extensively characterized and described in U.S. Pat. No. 7,223,761 B2.

5.2.1.4 Pharmaceutical Compositions and Precursors

One important difference between the provided solid pharmaceutical compositions and existing liquid-filled hard gelatin capsules is that the provided compositions are in substantially solid form. Accordingly, they can avoid problems associated with liquid-filled capsules, such as leakage of the capsules' contents. The provided compositions demonstrate comparable or improved stability and/or potency over known liquid-filled preparations.

Preferred salts and polymorphs of compound 101 for use in the pharmaceutical compositions are the Form I and Form II polymorphs of the besylate salt of compound 101.

The most preferred salt of compound 101 is benzenesulfonate, also called besylate.

The pharmaceutical compositions of the invention preferably comprise between about 0.1 mg and about 10.0 mg of benzenesulfonate (besylate) salt of the compound of formula (I).

The pharmaceutically acceptable excipients are selected from the groups consisting of solvents, wetting agents, diluents, fillers, superdisintegrants, binders, glidants, lubricants, and combinations thereof.

In particularly preferred embodiments, the pharmaceutically acceptable excipients are selected from the group consisting of sodium dodecyl sulfate, lactose monohydrate, microcrystalline cellulose, crospovidone, povidone, colloidal silicon dioxide, magnesium stearate, and combinations thereof. It should be understood that the invention contemplates use of other excipients that serve substantially the same functions in substantially the same manner as those described above.

In one embodiment, the pharmaceutical composition comprises the benzenesulfonate salt of the compound of formula (I), povidone, intragranular crospovidone, extragranular crospovidone, intragranular microcrystalline cellulose, extragranular microcrystal line cellulose, lactose monohydrate, and granulating water.

In a particularly preferred embodiment, the pharmaceutical composition is in the form of a powder, tablet, caplet or capsule, and comprises:

(1) the compound of formula (I) provided as the besylate salt thereof and constituting about 0.6 to 7.0 percent of the composition;

(2) lactose monohydrate constituting about 25% to about 35% of the composition;

(3) crospovidone constituting about 4% to about 5% of the composition;

(4) microcrystalline cellulose constituting about 50% to about 60% of the composition;

(5) povidone constituting about 1% to about 3% of the composition;

(6) optionally, colloidal silicon dioxide constituting up to about 0.7% of the composition;

(7) magnesium stearate constituting about 0.25% to about 1.5% of the composition.

wherein all percentages are percentages by weight.

In the above preferred formulation the weight ratio of intragranular microcrystalline cellulose to lactose monohydrate is from 1.8:1 to 0.67:1, and most preferably 1.5:1.

In accordance with the methods of the present invention, a precursor composition suitable for use in manufacturing the solid pharmaceutical composition is prepared by micronizing the active ingredient (preferably the besylate salt of compound 101) and performing wet granulation, wherein the compound is combined with pharmaceutically acceptable excipients to perform the precursor wet granules. A particularly preferred precursor composition for wet granulation comprises:

(a) about 0.5 to about 7.0% of the besylate salt of compound of formula (I)
(b) about 25% to 45% lactose monohydrate
(c) about 25% to about 45% microcrystalline cellulose;
(d) about 2% to 4% povidone;
(e) about 15% to about 24% water;

The ratio of component (c) to component (b) is preferably about 0.67:1 to 1.8:1, and most preferably about 1.5:1.

The amount of water used for granulation to prepare the above precursor composition is most preferably 18 to 21%, of the above-stated precursor composition.

The invention is further directed to the above precursor composition, after the water has been removed, for example by drying, to form a dry powder pre-cursor composition. In the above formulation, component (a) may be replaced with a combination comprising the compound of formula (I) and one or more anti-diabetic agents. Alternatively, additional anti-diabetic agents may be combined as extragranular materials, with the dried granulation mixture containing compound (I) as the only antidiabetic agent.

The final solid pharmaceutical composition, as well as the pre-cursor prepared via wet granulation can initially be in the form of a dry powder, prior to additional processing. The final pharmaceutical composition may then be formed into a tablet or provided as a capsule or caplet. The precursor may be combined with one or more additional extragranular excipients to form the solid dosage form of the pharmaceutical composition. Alternatively, the additional antidiabetic agent can be dry-blended with a powder that constitutes the final dried solid pharmaceutical composition containing compound 101. Alternatively the additional antidiabetic agent can be added in a dry blend as a separate layer of the formed tablet.

The pharmaceutical compositions provided herein can further include one or more pharmaceutically acceptable additives such as a suspending agent, a flavoring agent, a sweetening agent, a dispersing agent, a surfactant, a colorant, a solubilizer, a moistening agent, a plasticizer, a stabilizer, a penetration enhancer, an anti-foaming agent, an antioxidant, an preservative, or a mixture thereof.

5.2.1.5 Unit Dosage Forms

In certain embodiments, the pharmaceutical compositions comprise compound 101, including the salt forms and polymorphs of compound 101, in a unit dosage form.

In one embodiment, the invention provides a single unit dosage form suitable for oral administration to a human which comprises a micronized compound of formula (I):

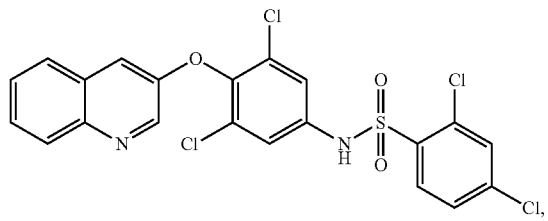 [SMILES: O=S(=O)(Nc1cc(Cl)c(Oc2cnc3ccccc3c2)c(Cl)c1)c1ccc(Cl)cc1Cl]

or a salt thereof, and at least one pharmaceutically acceptable excipient, binder or diluent, wherein said compound has mean particle size of about 1 to about 10 microns, wherein said dosage form after administration to a human provides an $AUC_{0 \to \infty}$ for the compound (I) of at least, or about, 150-5000 ng*hr/mL, a $T_{max}$ of less than about 5.0 hours, and wherein said dosage form is prepared using a wet granulation process.

In certain embodiments, dosage form after administration to a human provides a $T_{max}$ (the time after administration of a drug when the maximum plasma concentration is reached) of less than about 4.0 hours.

The pharmaceutical compositions provided herein may be formulated for administration to a subject via any conventional means including, but not limited to, oral, parenteral (e.g., intravenous, subcutaneous, or intramuscular), buccal, intranasal, rectal or transdermal administration routes.

The pharmaceutical compositions provided herein may be in a form suitable for oral administration, for example, as powders, tablets, pills, capsules, cachets, lozenges, and dispersible granules. Pharmaceutical compositions intended for oral use may contain one or more agents selected from the group consisting of sweetening agents, flavoring agents, coloring agents, preserving agents, binders, disintegrating agents, or an encapsulating material, in order to provide pharmaceutically elegant and palatable preparations.

In preferred embodiments, the unit dosage form is suitable for oral administration to a human as a tablet providing 0.5 to 5 milligrams compound 101.

5.2.1.5.1 Capsules and Tablets

In certain embodiments, the unit dosage form of the pharmaceutical compositions provided herein is in the form of a powder-filled capsule for oral administration.

The filling of the contents in the capsules can be performed using any capsule-filling technique known to those skilled in the art.

In certain embodiments, the unit dosage form of the pharmaceutical compositions provided herein is in the form of a tablet for oral administration.

Tablets may contain the solid active ingredient in admixture with at least one pharmaceutically acceptable excipient which is suitable for the manufacture of tablets. The excipient may be, for example; a disintegrating agent, such as a superdisintegrant; a binder; a diluent; a glidant; a lubricant; an emulsifier; or any other excipient known to one of skill in the art.

Preferred tablets are those which provide good potency, content uniformity, hardness, friability and dissolution, and which contribute to the chemical and physical stability of the pharmaceutical compositions.

The tablets described herein can be sized to hold the desired amount of a unit dosage, typically up to about 1 gram of the unit dosage.

5.2.1.5.2 Enteric Coating

The capsules, tablets or other unit dosage forms of the pharmaceutical compositions provided herein may also be coated with an enteric coating, alone or in addition to another coating. Enteric coating of pharmaceutical compositions that contain drugs is well known in the pharmaceutical sciences literature. See, for example, *Remington's Pharmaceutical Sciences*, 20$^{th}$ ed., Mack Publishing, Easton Pa. (2000), the contents of which is incorporated by reference in its entirety.

The enteric materials for use in the enteric coating preferably prevent release of the enteric-coated drug in gastric fluid of the stomach and prevent exposure of the drug to the acidity of the gastric contents while the enteric coated drug composition is in the stomach. After passing from the stomach into the intestine, the enteric coating preferably dissolves and releases the drug into intestinal fluids.

Materials suitable for use in the enteric coating include hydroxypropyl methylcellulose, hydroxyethyl cellulose, hydroxypropyl cellulose, methylcellulose, ethylcellulose, acrylic acid methacrylic acid ester copolymer, or a mixture thereof.

Additional materials suitable for use in the enteric coating include phthalates including hydroxypropyl methylcellulose phthalate, hydroxyethyl cellulose phthalate, hydroxypropyl cellulose phthalate, methylcellulose phthalate, ethylcellulose phthalate, and cellulose acetate phthalate.

In other embodiments of the pharmaceutical compositions provided herein, the capsule, tablet or other unit dosage form may additionally be coated with a controlled release coating, which is compatible with the other components of the enteric coating. The controlled release coating may comprise a hydrophobic controlled release material selected from an alkylcellulose, an acrylic polymer, or mixtures thereof.

5.2.2 Methods of Making

In a preferred embodiment, the solid pharmaceutical compositions of the invention are prepared using a wet granulation process.

In one aspect, the invention relates to a method of making a pharmaceutical composition for oral administration comprising a micronized compound of formula (I):

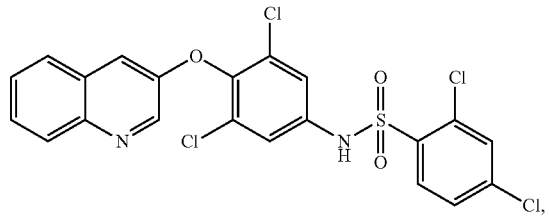

or a salt hereof, in a unit dosage form, wherein said method comprises the following steps:

(a) mixing micronized particles of the compound of formula (I) with one or more excipients to form an intragranular material;

(b) adding one or more granulation solutions to the intragranular material obtained in (a), and granulating the solution and intragranular material to form wet granules;

(c) drying the wet granules obtained in step (b) to form dry granules;

(d) milling the dry granules obtained in step (c);

(e) blending the milled dry granules obtained in step (d) with ext agranular material comprised of one or more excipients to form a blend; and (f) optionally, compressing the blend obtained in step (e) into a solid unit dosage form.

In certain embodiments, the mean particle size of the micronized compound 101, or a salt or polymorph thereof, is less than 20 microns.

In certain embodiments, the mean particle size of the micronized compound 101, or a salt or polymorph thereof, is about 1 to about 10 microns, about 1 to about 5 microns, or about 1 to about 3 microns.

In certain embodiments, the mean particle size of the micronized compound 101, or a salt or polymorph thereof, is about 1 to about 2 microns.

In some aspects of the invention, the excipients suitable for the provided methods are selected from the group consisting of sodium dodecyl sulfate, lactose monohydrate, microcrystalline cellulose, crospovidone, povidone, colloidal silicon dioxide, magnesium stearate, and combinations thereof. (Povidone is also commonly referred to as polypovidone.)

The excipient may be, for example, a disintegrating agent, such as a superdisintegrant; a diluent; a filler; a glidant; a lubricant; an emulsifier, such as a surfactant or wetting agent; or any other excipient known to one of skill in the art.

In certain embodiments, the disintegrating agent is a superdisintegrant. In certain embodiments, the disintegrating agent is a cross-linked polyvinylpyrrolidone or cross-linked polyvinylpolypyrrolidone. In certain embodiments, the disintegrating agent is crospovidone. In certain embodiments, the superdisintegrant is crospovidone.

In certain embodiments, the glidant is a fumed silica. In certain embodiments, the glidant is colloidal silicon dioxide.

In certain embodiments, the lubricant is magnesium stearate.

In certain embodiments, the emulsifier is wetting agent. In certain embodiments, the wetting agent is sodium dodecyl sulfate.

In certain embodiments, the binder is polyvinylpyrrolidone (also known as povidone.)

In a preferred embodiment, the method comprises the additional step of: (i) adding a granulating solution to the wet granules obtained in step (b) to form wet granules of different composition than those obtained in step (b); wherein the granulating solution added in this additional step is the same or different from the granulating solution added in step (b). In a particularly preferred embodiment, a granulating solution added in step (b) comprises at least about 20% w/w povidone in water, and the granulating solution added in the above-referenced additional step comprises povidone or another binder, or can be water that is substantially free of povidone, or water that is substantially free of substances other than water (e.g., purified water).

In a preferred embodiment, the binder comprises about, or greater than, 20% w/w povidone in water. It was surprisingly found that tablets manufactured by a wet granulation process wherein the binder comprises about, or greater than 20% povidone w/w in water, have potency of at least about 95.0%, which is higher potency than found in the tablets manufactured with lesser amounts of povidone. Without wishing to be bound to any specific theory, it is believed that the achievement of higher potency is based on the unexpected discovery herein that sufficiently high binder (e.g., povidone) concentration is critical to sufficiently wet the active pharmaceutical ingredient (API) particles in the mixture and therefore, incorporate them in the granulation. It is believed that when povidone (or other binder) is not present at sufficiently high concentration, the API particles are inadequately bound in the wet granulation and therefore selectively lost during the drying process, contributing to a loss in potency.

The wet granulation process may have the following advantages over other processes of making pharmaceutical compositions: increasing the uniformity of the solid active ingredient in the pharmaceutical compositions; producing highly porous granules of the solid active ingredient which can disintegrate rapidly in an aqueous solution, leading to rapid release of the solid active ingredient from the pharmaceutical compositions. These advantages improve the dissolution of the pharmaceutical compositions, which is believed to contribute to improved bioavailability.

5.2.3 Methods of Treatment

In yet another aspect, provided herein are methods of treating PPARγ-mediated conditions or diseases by administering to a subject having such a disease or condition, a therapeutically effective amount of the solid pharmaceutical composition comprising a salt or polymorph of compound 101, as provided herein. The subject can be an animal such as, for example, a mammal, including, but not limited to, a primate (e.g., a human), a cow, a sheep, a goat, a horse, a dog, a cat, a rabbit, a rat, a mouse, and the like.

Depending on the biological environment (e.g., cell type, pathological condition of the host, etc.), these pharmaceutical compositions can activate or block the actions of PPARγ. By activating, i.e., agonizing, the PPARγ receptor, the pharmaceutical compositions will find use as therapeutic agents capable of modulating conditions mediated by the PPARγ receptor, e.g. Type 2 Diabetes. Additionally, the pharmaceutical compositions can be useful for the prevention and treatment of complications of diabetes (e.g., neuropathy, retinopathy, glomerulosclerosis, and cardiovascular disorders), and preventing or treating hyperlipidemia. Still further, the pharmaceutical compositions can be useful for the modulation of inflammatory conditions which most recently have been found to be controlled by PPARγ. (See, Ricote et al., 1998, *Nature* 391:79-82, and Jiang et al., 1998, *Nature* 391:82-86.) Examples of inflammatory conditions include rheumatoid arthritis and atherosclerosis. Pharmaceutical compositions that act via antagonism of PPARγ can be useful for treating obesity, hypertension, hyperlipidemia, hypercholesterolemia, hyperlipoproteinemia, and metabolic disorders.

In therapeutic use for the treatment of obesity, diabetes, inflammatory conditions or other conditions or disorders mediated by PPARγ, the salts or polymorphs of compound 101 can be administered as the pharmaceutical compositions provided herein at the initial dosage of about 0.001 mg to about 100 mg daily. A daily dose range of about 0.1 mg to about 10 mg is preferred. A daily dose range of about 0.5 mg to about 5 mg is particularly preferred. The dosages, however, may be varied depending upon the requirements of the patient, the severity of the condition being treated, and the compound being employed. Determination of the proper dosage for a particular situation is within the skill of the practitioner. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day, if desired.

In the treatment or prevention of conditions which require PPARγ receptor modulation an appropriate dosage level will generally be about 0.001 to 100 mg salt or polymorph of compound 101 per day which can be administered in single or multiple doses of the oral pharmaceutical preparation provided herein. Preferably, the dosage level will be about 0.01 to about 25 mg per day; more preferably about 0.1 to about 10 mg per day; and particularly preferably about 0.5 to about 5.0 mg per day. A suitable dosage level may be about 0.01 to 25 mg per day, about 0.1 to 10 mg per day, or about 0.5 to 5 mg per day. Within this range the dosage may be 0.005 to 0.05, 0.05 to 0.5, or 0.5 to 5.0 mg per day. The pharmaceutical compositions provided herein are preferably provided in the form of ingestible capsules containing 0.1 to 20 milligrams of the salt or polymorph of compound 101, particularly 0.1, 0.2, 0.3, 0.4, 0.5, 0.6, 0.7, 0.8, 0.9, 1.0, 1.2, 1.4, 1.5, 1.6, 1.8, 2.0, 2.2, 2.4, 2.5, 2.6, 2.8, 3.0, 3.2, 3.4, 3.5, 3.6, 3.8, 4.0, 4.2, 4.4, 4.5, 4.6, 4.8, 5.0, 5.5, 6.0, 6.5, 7.0, 7.5, 8.0, 8.5, 9.0, 9.5, 10.0, or 20.0 mg of the salt or polymorph of compound 101 for the symptomatic adjustment of the dosage to the patient to be treated. The pharmaceutical compositions provided herein may be administered on a regimen of 1 to 4 times per day, preferably once or twice per day.

It will be understood, however, that the specific dose level and frequency of dosage for any particular patient may be varied and will depend upon a variety of factors including, for example, the activity of the specific polymorph employed, the metabolic stability and length of action of that polymorph, the age, body weight, general health, sex, diet, mode and time of administration, rate of excretion, drug combination, and the severity of the patient's condition.

The pharmaceutical compositions provided herein can be combined with other compounds having related utilities to treat or prevent metabolic disorders and inflammatory conditions, complications thereof and pathologies associated therewith (e.g., cardiovascular disease and hypertension). In many instances, administration of the subject pharmaceutical compositions in conjunction with these alternative agents enhances the efficacy of such agents. Accordingly, in some instances, the present pharmaceutical compositions, when combined or administered in combination with, e.g., anti-diabetic agents, can be used in dosages which are less than the expected amounts when used alone, or less than the calculated amounts for combination therapy.

Thus, provided herein is a pharmaceutical composition for oral administration, in solid form, comprising: micronized compound 101, or a salt or polymorph thereof, in a unit dosage form, wherein the mean particle size of compound 101, or a salt or polymorph thereof, is less than 20 microns; and an alternative agent.

In certain embodiments, the pharmaceutical compositions provided herein may be used to treat or prevent a variety of other indications. Such indications include, but are not limited to, metabolic conditions such as diabetes (including type I and Type 2 diabetes), hypertension, angina pectoris, dyslipidemia (including hypertriglyceridemia, hyperlipoproteinemia, and hypercholesterolemia), gout, nephropathy and other renal diseases secondary to diabetes, diabetic neuropathy, other insulin-resistance-related diseases, polycystic ovarian syndrome, glucocorticoid-induced insulin resistance, obesity, bone disorders, female-specific conditions (including excessive climacteric uterine bleeding), and acne; neurological disorders such as Alzheimer's disease, neuroinflammation, ischemic stroke, closed-head injury, and multiple sclerosis; proliferative disorders such as atherosclerosis, restenosis, colon cancer, prostate cancer, breast cancer, liposarcoma, epithelial cell cancers, uroepithelial cancer, and other cancers; and inflammatory or immune disorders such as rheumatoid arthritis, inflammatory bowel disease, colitis, Crohn's disease, macular degeneration, other inflammatory disorders, and other immune disorders. Rationales suggesting the utility of the pharmaceutical compositions provided herein for treating or preventing such indications are discussed in detail in U.S. Pat. No. 7,223,761.

In particularly preferred embodiments, the pharmaceutical compositions provided herein are directed to the treatment or prevention of Type 2 Diabetes using a salt or polymorph of compound 101, either alone or in combination with a second therapeutic agent selected from anti-diabetic agents such as insulin, sulfonylureas (e.g., meglinatide, tolbutamide, chlorpropamide, acetohexamide, tolazamide, glyburide, glipizide, and glimepiride), biguanides, metformin (Glucophage®), α-glucosidase inhibitors (acarbose), thiazolidinone compounds. e.g., rosiglitazone (Avandia®), troglitazone (Rezulin®), and pioglitazone (Actos®). When used in combination, the practitioner can administer a combination of the therapeutic agents, or administration can be sequential.

6. EXAMPLES

Reagents and solvents used below can be obtained from commercial sources such as Aldrich Chemical Co. (Milwaukee, Wis., USA). $^1$H-NMR spectra were recorded on a Varian Gemini 400 MHz NMR spectrometer. Significant peaks are tabulated in the order: number of protons, multiplicity (s, singlet; d, doublet; t, triplet; q, quartet; m, multiplet; br s, broad singlet) and coupling constant(s) in Hertz (Hz). Electrospray ionization (ESI) mass spectrometry analysis was conducted on a Hewlett-Packard 1100 MSD electrospray mass spectrometer using the HP 1100 HPLC for sample delivery.

Mass spectrometry results are reported as the ratio of mass over charge. The compound was dissolved in methanol at 0.1 mg/mL and 1 microliter was infused with the delivery solvent into the mass spectrometer, which scanned from 100 to 1500 daltons. The compound could be analyzed in the positive ESI mode, using 1:1 acetonitrile/water with 1% acetic acid as the delivery solvent. The compound could also be analyzed in the negative ESI mode, using 2 mM NH$_4$OAc in acetonitrile/water as delivery solvent.

6.1 Example 1: Formulations

6.1.1 Wet Granulation Formulations

This example illustrates five wet granulation tablet formulations of the micronized besylate salt of compound 101, which were made and tested for chemical and physical stability, dissolution, and bioavailability (see Examples 2 and 3, below). These five formulations (F6-F10) are presented in Table 1.A (illustrating the wet granulation precursor of the invention prior to removal of water) and Table 1.B (illustrating a dry power/tablet formulation of the invention).

TABLE 1.A

Wet Granulation Formulation of Besylate Salt of Compound 101--Prior to Removal of Water

| Component [1] | Function | Tablet Lot (% w/w of wet granulation) | | | | |
|---|---|---|---|---|---|---|
| | | 58-76 F6 | 115-133 F7 | 172-190 F8 | 191-209 F9 | 229-247 F10 |
| INT131 besylate [2] | Active | 0.63 | 6.32 | 6.32 | 0.59 | 5.86 |
| Lactose monohydrate | Diluent | 44.68 | 42.72 | 42.24 | 41.22 | 26.81 |
| Microcrystalline cellulose (Avicel PH101) | Diluent and disintegrant | 29.93 | 28.62 | 28.13 | 27.49 | 40.21 |
| Ratio of microcrystalline cellulose:Lactose Monohydrate | | 0.67:1 | 0.67:1 | 1.5:1 | 0.67:1 | 0.67:10 |
| Sodium dodecyl sulfate | Wetting agent | 0 | 0.96 | 0 | 1.79 | 0 |
| Crospovidone | Disintegrant | 2.89 | 1.45 | 1.45 | 1.34 | 1.34 |
| Povidone | Binder | 3.86 | 1.93 | 3.86 | 3.58 | 1.79 |
| Microcrystalline cellulose (Avicel PH102) | Diluent and disintegrant | ** | ** | ** | ** | ** |
| Crospovidone | Disintegrant | ** | ** | ** | ** | ** |
| Colloidal silicon dioxide | Glidant | ** | ** | ** | ** | ** |
| Magnesium stearate | Lubricant | ** | ** | ** | ** | ** |
| Purified water [3] | Granulation fluid | 18 | 18 | 18 | 24 | 24 |
| mixing time (min) | | 1 | 3 | 1 | 3 | 1 |
| mixing speed (rpm) | | 300 | 200 | 300 | 200 | 300 |
| | Total | 100 | 100 | 100 | 100 | 100 |

[1] All inactive components are USP-NF grade
[2] Quantities are for INT131 besylate salt and are equivalent to 0.5, 3 and 5 mg per tablet INT131 free base
[3] Removed during manufacturing process
** Ingredients not present in wet granulation, added as extragranular excipients after drying of wet granules (see Table 1B below)

TABLE 1B

Final Tablet Formulations (dry solid) of Besylate Salt of Micronized Besylate Salt of Compound 101

| Component [1] | Function | Tablet Lot (mg per tablet) | | | | |
|---|---|---|---|---|---|---|
| | | 58-76 F6 | 115-133 F7 | 172-190 F8 | 191-209 F9 | 229-247 F10 |
| *INT131 besylate [2] | Active | 0.655 | 6.55 | 6.55 | 0.655 | 6.55 |
| *Lactose monohydrate | Diluent | 46.31 | 44.28 | 43.79 | 46.10 | 29.98 |
| *Microcrystalline cellulose (Avicel PH101) | Diluent and disintegrant | 31.03 | 29.67 | 29.16 | 30.75 | 44.97 |
| *Sodium dodecyl sulfate | Wetting agent | 0 | 1.0 | 0 | 2.0 | 0 |
| *Crospovidone (intragranular) | Disintegrant | 3.0 | 1.5 | 1.5 | 1.5 | 1.5 |
| *Povidone | Binder | 4.0 | 2.0 | 4.0 | 4.0 | 2.0 |
| Microcrystalline cellulose (Avicel PH102)** | Diluent and disintegrant | 10.5 | 10.5 | 12.0 | 10.5 | 12.0 |
| Crospovidone (extragranular)** | Disintegrant | 3.0 | 3.0 | 1.5 | 3.0 | 1.5 |
| Colloidal silicon dioxide** | Glidant | 0.5 | 0.5 | 0.5 | 0.5 | 0.5 |
| Magnesium stearate** | Lubricant | 1.0 | 1.0 | 1.0 | 1.0 | 1.0 |
| Purified water [3] | Granulation fluid | 0 | 0 | 0 | 0 | 0 |
| | Total | 100.0 | 100.0 | 100.0 | 100.0 | 100.0 |

[1] All inactive components are USP-NF grade
[2] Quantities are for INT131 besylate salt and are equivalent to 0.5, 3 and 5 mg per tablet INT131 free base
[3] Removed during manufacturing process
*Intragranular materials
***Ingredients added as extragranular material after drying of formulation of Table 1.A All five formulation (F6-F10) achieved initial potency near target, with no degradation; no degradation was observed at test points up to 4 weeks at 2-8° C., 25° C./60% RH or 40° C./75% RH.

For comparative purposes, Table 2, below, illustrates two dry blend and three hot-melt capsule formulations of the besylate salt of compound 101, which were made and tested for chemical and physical stability, dissolution, and bioavail ability (see Examples 2 and 3, below). These five formulations (F1-F5) are presented in Table 2.

TABLE 2

Comparative: Dry Blend and Hot-Melt Capsule Formulations of the Besylate Salt of Compound 101

| Component | Formulation (% w/w per capsule)[†] | | | | |
|---|---|---|---|---|---|
| | F1 (dry blend) | F2 (dry blend) | F3 (hot-melt) | F4 (hot-melt) | F5 (hot-melt) |
| Besylate salt of compound 101* | 1.31 | 1.31 | 1.31 | 1.31 | 1.31 |
| ProSolv ® | 95.1 | 85.1 | 85.1 | 85.1 | 85.1 |
| Crospovidone | 3 | 3 | 3 | 3 | 3 |
| Magnesium stearate | 0.5 | 0.5 | 0.5 | 0.5 | 0.5 |
| Fumed Silica | 0.1 | 0.1 | 0.1 | 0.1 | 0.1 |
| Poloxamer | | 10 | | | |
| Gelucire ® | | | 10 | | |
| Vitamin E TPGS | | | | 10 | |
| Solutol ® | | | | | 10 |

*1.31% besylate salt of compound 101 is equivalent to 1.00% free base of compound 101
[†]approx. mg/capsule The five hot-melt and dry blend formulations (F1-F5) achieved initial potency near target, with no degradation; no degradation was observed at test points up to 4 weeks at 2-8° C., 25° C./60% RH or 40° C./75% RH. However the dry blends and hot melts did not provide satisfactory dissolution (see Example 2, below).

6.2 Example 2: Dissolution Testing

6.2.1 Dissolution Testing Wet Granulation Tablet Formulations

Dissolution testing was performed with a USP Type 2 apparatus with paddles, at 75 rpm, 37° C., 900 mL (sink condition), 2% SDS in pH 1.5 (with HCl). FIG. 1 provides the dissolution testing results of the besylate salt of compound 101 of the five formulations (F6-F10) of Example 1.

6.2.2 Comparative: Dissolution Testing of Dry Blend and Hot-Melt Capsule Formulations Dissolution testing was performed on hot melt and dry blend formulation of Compound 101. (Note: in this comparative section, a besylate salt of compound 101 in a liquid-filled oil based capsule (see U.S. Provisional Patent Application No. 61/102,658) was used as a control). The results of the dissolution testing are presented in FIG. 2. Relative dissolution at 60 minutes was: F0 (oil-based liquid-filled capsule as comparator), F3 (hot-melt with Gelucire®), F5 (hot-melt with Solutol®)>F4 (hot-melt with Vitamin E TPGS)>F1, F2 (dry blends with and without poloxamer)>dry powder of 100% besylate salt of compound 101.

6.2.3 Comparison Between the Inventive Formulations vs Dry Blend and Hot-Melt Capsule Formulations Comparison of the data in FIG. 1 and FIG. 2 demonstrates markedly superior dissolution (FIG. 1) in the compositions prepared according to the present invention. The data further demonstrates that the solid formulations of the present invention achieve greater and faster dissolution compared to the liquid-filled capsule disclosed in U.S. Provisional Patent Application 61/102,658. (See FIG. 2.)

6.3 Example 3: Pharmacokinetics

6.3.1 Wet Granulation Tablet Formulations

The single-dose pharmacokinetics of the five wet granulation tablet formulations (F6-F10) and the oil-based capsule formulation described above (F0) were evaluated in fasted cynomolgus monkeys in a 3-way crossover design, where six monkeys were each dosed with three of the six formulations. The primary parameter of comparison was AUC. The results are presented in FIG. 5 and Table 3.

TABLE 3

Relative Bioavailability (AUC) of Wet Granulation Tablet Formulations of the Micronized Besylate Salt of Compound 101

| | F6 | F7 | F8 | F9 | F10 |
|---|---|---|---|---|---|
| Relative Bioavailability ($[AUC_{0-24}]/[AUC_{0-24}]_{control}$ Dose Normalized) | 65% | 73% | 77% | 53% | 43% |

FIG. 5 and Table 3 demonstrate that the amount of granulating water has a strong effect on bioavailability. Samples F6, F7 and F8 (having water content in the wet granulation precursor of 18%) provided better bioavailability in the finished formulation than samples F9 and F10 (having 24% water in the wet granulation precursor).

Further, it was observed that the diluent ratio (intragranular microcrystalline cellulose to lactose monohydrate) affected compressibility index and particle size of the dry granulation and the final blend compressed into the tablet, with a higher ratio (1.5:1) preferable overall.

6.3.2 Comparative: Dry Blend and Hot-Melt Capsule Formulations

The single-dose pharmacokinetics of the two dry blend capsule formulations (F1, F2), the three hot-melt capsule formulations (F3-F5) and the oil-based, liquid-filled capsule formulation described above (F0) were tested in fasted cynomolgus monkeys in a 3-way crossover design, where six monkeys were each dosed with three of the six formulations. The primary parameter of comparison was the AUC. The results are presented in FIG. 3.

FIG. 4 presents an in vitro-in vivo correlation (IVIVC) between bioavailability in the monkey and dissolution at 60 minutes. A correlation of r=0.917 suggests that improving dissolution of the formulation may contribute to improved bioavailability.

Dissolution testing was performed on all formulations after storage for 4 weeks at 2-8° C., 25° C./60% RH or 40° C./75% RH. Dry blend Formulations 1 and 2 demonstrated an increase in dissolution rate with storage. Gelucire Formulation 3, which demonstrated the most rapid dissolution initially, exhibited a decrease in dissolution rate upon storage. The cause was investigated and tentatively assigned to a crystal form change of the Gelucire component during storage (i.e., lack of stability).

The Gelucire formulation was manufactured at a 250-g scale, at 1- and 6-mg capsule strengths, under GMP conditions. The manufacture included a curing step (holding at 40° C. for several hours) to drive the crystal form change to completion. Uncured capsules were set aside for comparison. The cured capsules dissolved more rapidly than the uncured capsules for one strength, which was inconsistent with crystal form change theory.

6.3.3 Comparison Between the Inventive Formulations vs Dry Blend and Hot-Melt Capsule Formulations The inventive formulations demonstrated much better bioavailability than dry blend formulations. While hot-melt capsule formulations had acceptable bioavailability, they were generally found to be physically unstable, which was unexpected and surprising.

Accordingly, the inventive formulations were demonstrated to be significantly and unexpectedly superior to dry blend and hot melt formulations.

6.4 Example 4: Formulation Selection and Further Testing

This example illustrates optimization of select wet granulation tablet formulations of the besylate salt of compound 101 which were further tested.

Formulation F8 (18% granulating water and 1.5:1 diluent ratio) demonstrated the highest relative bioavailability according to Table 3 above, and F10 (24% granulating water and 0.67:1 diluent ratio) demonstrated the lowest relatively bioavailability according to Table 3 above.

Four wet granulation tablet formulations containing 18 or 21% granulating water and 1.5:1 or 1.2:1 diluent ratio were manufactured at both low (0.655 mg) and high (6.55 mg) concentrations of compound (I); based upon chemical and physical assessments, Formulation A, comprising 18% granulating water, 1.5:1 diluent ratio, and 0.65% w/w or 6.55% w/w of the besylate salt of compound 101; and Formulation B, comprising 21% granulating water, 1.2:1 diluent ratio, and 0.655% w/w or 6.55% w/w of the besylate salt of compound 101. Formulations A and B are presented in Table 4.

TABLE 4

Wet Granulation Tablet Formulations A and B of the Micronized Besylate Salt of Compound 101

| Component | Formulation A | Formulation B |
|---|---|---|
| Besylate salt of compound 101* | 0.655 or 6.55 mg† | 0.655 or 6.55 mg |
| Diluent ratio of Microcrystalline cellulose versus lactose monohydrate | 1.5:1 | 1.2:1 |
| Granulating water | 18% % w/w per tablet | 21% % w/w per tablet |

*1.31 mg besylate salt of compound 101 is equivalent to 1.00 mg free base of compound 101
†approx. % w/w per tablet

TABLE 5

FORMULATIONS "A" AND "B" OF THE INVENTION

| Component [1] | Function | Tablet Strength (mg/tablet) | | | |
|---|---|---|---|---|---|
| | | A-0.5 | A-5 | B-0.5 | B-5 |
| INT131 besylate [2] (intragranular) | Active | 0.655 | 6.55 | 0.655 | 6.55 |
| Lactose monohydrate (intragranular) | Diluent | 32.34 | 29.99 | 36.75 | 34.08 |
| Microcrystalline cellulose (Avicel PH101) (intragranular) | Diluent and disintegrant | 48.51 | 44.96 | 44.10 | 40.87 |
| Crospovidone (intragranular) | Disintegrant | 1.5 | 1.5 | 1.5 | 1.5 |
| Povidone (intragranular) | Binder | 2.0 | 2.0 | 2.0 | 2.0 |
| Microcrystalline cellulose (Avicel PH102) (extragranular) | Diluent and disintegrant | 10.5 | 10.5 | 10.5 | 10.5 |
| Crospovidone (extragranular) | Disintegrant | 3.0 | 3.0 | 3.0 | 3.0 |
| Colloidal silicon dioxide (extragranular) | Glidant | 0.5 | 0.5 | 0.5 | 0.5 |
| Magnesium stearate (extragranular) | Lubricant | 1.0 | 1.0 | 1.0 | 1.0 |
| Purified water [3] | Granulation fluid | 0 | 0 | 0 | 0 |
| Total | | 100.0 | 100.0 | 100.0 | 100.0 |

[1] All inactive components are USP-NF grade.
[2] Quantities are for INT131 besylate salt and are equivalent to 0.5, 3 and 5 mg per tablet INT131 free base.
[3] Removed during manufacturing process.

Formulas A and B achieved initial potency near target, with no degradation. Further, Formulas A and B exhibited good tablet properties, for example, good appearance, content uniformity, dissolution, hardness, and friability.

The single-dose pharmacokinetics of Formulas A and B and the oil-based capsule formulation described above (F0) were evaluated in fasted cynomolgus monkeys. The primary parameters of comparison were AUC and $T_{max}$. The results are presented in FIG. 6 and Table 6.

TABLE 6

Relative Bioavailability (AUC) and $T_{max}$ of Formulations A and B of the Besylate Salt of Compound 101

| Formulation | F0 | Formulation A | | | | Formulation B | | |
|---|---|---|---|---|---|---|---|---|
| besylate salt of compound 101 | 1.31 mg† | 0.655 mg | 3.28 mg (5 × 0.655) | | 6.55 mg | 0.655 mg | 3.28 mg (5 × 0.655) | 6.55 mg |
| Relative Bioavailability ($[AUC_{0-24}]$/ $[AUC_{0-24}]_{control\ Dose\ Normalized}$) | 100 ± 16% | 110% | 73% 91 ± 20% | | 90% | 86% | 92% 83 ± 18% | 71% |
| $T_{max}$ (hours) | 3.3 | | 3.5 | | | | 3.8 | |

* 1.31 mg besylate salt of compound 101 is equivalent to 1.00 mg free base of compound 101
†approx. % w/w per tablet As can be seen in FIG. 6 and Table 6, Formulations A and B show surprisingly good pharmacokinetics, and support the use of these formulations for the treatment of the disclosed indications.

6.5 Example 5: Tablet Manufacturing Process

This example illustrates an exemplary manufacturing process for a tablet of the besylate salt of compound 101.

Micronized particles of the besylate salt of compound 101 were screened and mixed with crospovidone, microcrystalline cellulose (PH101), and lactose monohydrate in a Quadro Comil U10 Mill® to form an intragranular material. The intragranular material was then fed into a 25 L Diosna P25 High Shear Mixer/Granulator® to which two granulating solutions were successively added, with mixing, to form wet granules. The first granulating solution (20% w/w povidone in granulating water) was added, with mixing, to form wet granules. The second granulating solution (granulating water without povidone) was then added, with mixing, to the wet granules until the povidone concentration in the wet granules was reduced to the equivalent of 13% w/w povidone in granulating water. The resulting wet granules were then dried in a 20 L fluid air bed dryer, and the dried granules milled in a FitzMill M5A® communitor. The milled dry granules were blended with crospovidone, microcrystalline cellulose (PH102), colloidal silicon dioxide, and magnesium stearate in an 8-qt. PK-V blender to form a final blend, which was compressed into tablets.

The above manufacturing process is illustrated in FIG. 7, showing in-process quality control at the drying, blending and compressing steps.

6.6 Example 6: Optimization of Binder and Granulation Solution

This example illustrates, for a preferred embodiment of the invention, that the amount of binder in the granulation solution can affect potency in the final pharmaceutical composition of the present invention, and further illustrates the manner in which granulation solutions are preferably applied in a multi-step fashion.

Table 7 illustrates that tablets manufactured by a wet granulation process wherein the binder comprises at least about 15% povidone w/w in water, have potency of at least about 95.0%, which is higher potency than found in the tablets manufactured with a lower concentration of povidone in the granulating water.

Another potentially important difference between the methods of the present invention and conventional wet granulation manufacturing process is that in a conventional process, only one binder solution containing the full amounts of binder and granulating water is employed.

TABLE 7

EFFECT OF BINDER ADDITION METHOD ON POTENCY

| Formulation | Tablet Strength (mg) | Lot Size (kg) | Binder (povidone) Addition Method | Potency (% of target) |
|---|---|---|---|---|
| A | 0.5 | 0.71 | 20% solution | 98.8 |
| A | 5 | 0.71 | 20% solution | 96.7 |
| A | 0.5 | 3.60 | 13% solution | 93.4 |
| A | 5 | 4.25 | 9.7% solution | 92.8 |
| A | 0.5 | 4.25 | 20% solution | 95.5 |
| A | 3 | 4.25 | 20% solution | 97.7 |
| A | 5 | 4.25 | 20% solution | 100.7 |

Accordingly, the inventive formulations manufactured by a wet granulation process wherein the binder comprises at least about 20% povidone w/w in water, have potency of at least about 95.0%, which is higher potency than found in the tablets manufactured with lesser amounts of povidone.

All publications and patent applications cited in this specification are herein incorporated by reference as if each individual publication or patent application were specifically and individually indicated to be incorporated by reference. Although the foregoing has been described in some detail by way of illustration and example for purposes of clarity of understanding, it will be readily apparent to those of ordinary skill in the art in light of the teachings of the specification that certain changes and modifications may be made thereto without departing from the spirit or scope of the appended claims.

What is claimed is:

1. A pharmaceutical composition, in solid form, suitable for oral administration to a subject, which comprises a compound of formula (I):

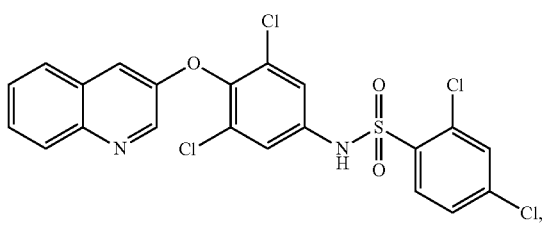 [SMILES: O=S(=O)(Nc1cc(Cl)c(Oc2cnc3ccccc3c2)c(Cl)c1)c1ccc(Cl)cc1Cl]

(I)

or a salt thereof, wherein the composition comprises
(1) the compound of formula (I) provided as the benzenesulfonate (besylate) salt thereof and constituting about 0.6 to 7.0 percent of the composition;
(2) lactose monohydrate constituting about 25% to about 35% of the composition;
(3) crospovidone constituting about 4% to about 5% of the composition;
(4) microcrystalline cellulose constituting about 50% to about 60% of the composition;
(5) povidone constituting about 1% to about 3% of the composition;
(6) optionally, colloidal silicon dioxide constituting up to about 0.7% of the composition;
(7) magnesium stearate constituting about 0.25% to about 1.5% of the composition, wherein all percentages are percentages by weight based on the total weight of the composition.

2. The solid pharmaceutical composition of claim 1 in the form of a tablet or powder.

3. The solid pharmaceutical composition of claim 1 provided as a unit dosage form.

4. The solid pharmaceutical composition of claim 1 prepared by a process which comprises the steps of (a) micronizing the compound of formula (I); and (b) preparing a wet granulation of the micronized compound in combination with one or more pharmaceutically acceptable excipients.

5. The solid pharmaceutical composition of claim 1, wherein the mean particle size of the compound of formula (I) is selected from the group consisting from less than 150 microns, less than 100 microns, less than 50 microns, less than 20 microns, and about 1 to about 10 microns.

6. The solid pharmaceutical composition of claim 2 wherein the benzenesulfonate salt is present in an amount of between about 0.1 to about 10.0 mg.

7. A method of making the solid pharmaceutical composition of claim 1, wherein said pharmaceutical composition is made by wet granulation.

8. The method of claim 7 comprising the steps of:
(a) mixing micronized particles of the compound of formula (I) with one or more excipients to form a powder blend;
(b) adding a granulating solution to the powder blend obtained in step (a), and mixing the solution and powder blend to form wet granules;
(c) drying the wet granules obtained in step (b) to form dry granules;
(d) milling the dry granules obtained in step (c);
(e) blending the milled dry granules obtained in step (d) with one or more excipients to form a blend constituting the final composition of the solid pharmaceutical composition; and
(f) optionally, compressing the blend obtained in step (e) into a unit dosage form.

9. A solid pharmaceutical composition suitable for unit dosage administration to a human, comprising the pharmaceutical composition prepared by the method of claim 8.

10. A method of treating a PPARγ-mediated condition or disorder in a human, the method comprising administering to the subject a therapeutically effective amount of the solid pharmaceutical composition of claim 1.

11. The solid pharmaceutical composition of claim 2, wherein said powder comprises an encapsulated powder.

12. The solid pharmaceutical composition of claim 1, wherein the ratio of microcrystalline cellulose to lactose monohydrate is about 1.4:1 to 1.7:1.

13. The solid pharmaceutical composition of claim 1, wherein the ratio of microcrystalline cellulose to lactose monohydrate is about 1.5:1.

14. The solid pharmaceutical composition of claim 1, wherein the solid pharmaceutical composition, after administration to a subject, is capable of providing in the subject an $AUC_{0\rightarrow\infty}$ for the compound (I) of about 150 to about 5000 ng*hr/mL.

15. The solid pharmaceutical composition of claim 1, wherein the solid pharmaceutical composition, after administration to a subject, is capable of providing in the subject an $AUC_{0\rightarrow\infty}$ for the compound (I) from about 5000 to about 35,000 ng*hr/mL.

16. The solid pharmaceutical composition of claim 1, wherein the solid pharmaceutical composition, after administration to a subject, is capable of providing in the subject a $T_{max}$ of less than 4.0 hours.

* * * * *